(12) United States Patent
van Zon et al.

(10) Patent No.: US 11,845,407 B1
(45) Date of Patent: Dec. 19, 2023

(54) CART CLEANING MACHINE

(71) Applicant: Alliance Manufacturing, Inc., Fond du Lac, WI (US)

(72) Inventors: David Nicholas van Zon, Rosendale, WI (US); John Michael Wehner, Fond du Lac, WI (US); Jason Daniel Krug, Fond du Lac, WI (US); Kenneth John Manninen, Fond du Lac, WI (US)

(73) Assignee: Alliance Manufacturing, Inc., Fond du Lac, WI (US)

( * ) Notice: Subject to any disclaimer, the term of this patent is extended or adjusted under 35 U.S.C. 154(b) by 162 days.

(21) Appl. No.: 17/532,683

(22) Filed: Nov. 22, 2021

Related U.S. Application Data

(60) Provisional application No. 63/117,322, filed on Nov. 23, 2020.

(51) Int. Cl.
*B60S 3/04* (2006.01)
(52) U.S. Cl.
CPC ........................................ *B60S 3/04* (2013.01)
(58) Field of Classification Search
CPC ..... B60S 3/00–066; B08B 3/02; B08B 3/022; B08B 3/024
See application file for complete search history.

(56) References Cited

U.S. PATENT DOCUMENTS

| | | | |
|---|---|---|---|
| 3,444,867 A | 5/1969 | Thornton | |
| 4,279,263 A | 7/1981 | Pulliam | |
| 4,711,257 A | 12/1987 | Kobayashi | |
| 6,090,218 A | 7/2000 | Brackmann et al. | |
| 6,427,707 B1 | 8/2002 | Morris | |
| 7,258,125 B2 | 8/2007 | Holbrook | |
| 2002/0144366 A1* | 10/2002 | Ikari | B60S 3/06 134/123 |
| 2005/0005949 A1* | 1/2005 | Boggess | A47L 1/08 15/103 |
| 2005/0121057 A1 | 6/2005 | Knowlton et al. | |
| 2005/0214159 A1 | 9/2005 | Schwei et al. | |
| 2006/0011220 A1 | 1/2006 | Mueller | |

(Continued)

FOREIGN PATENT DOCUMENTS

| | | | | |
|---|---|---|---|---|
| EP | 2284053 B1 * | 10/2014 | ............ | B05B 13/02 |
| KR | 100893790 | 4/2009 | | |

OTHER PUBLICATIONS

EP2284053B1 Machine Translation (Year: 2014).*

*Primary Examiner* — Spencer E. Bell
(74) *Attorney, Agent, or Firm* — Brannen Law Office, LLC

(57) ABSTRACT

A cart cleaning machine has a foundation, a dock, a movable gantry, and a bellow assembly. The foundation has a cart path spanning the length of the foundation between a first end and a second end. Two side channels are also provided. A dock is stationarily mounted to the foundation. The dock has the shape of an inverted U to allow carts to pass through. The dock has a controller, a water inlet, an electrical hookup, a chemical station, and line management devices. The movable gantry is movable with respect to the foundation. It has a drive mechanism with sprockets that interact with bands spanning between the foundation ends. The gantry has spray nozzles and blow off openings. The bellow assembly is between the dock and the gantry. Water and electric lines pass through the bellow assembly and span between the dock and movable gantry.

11 Claims, 30 Drawing Sheets

(56) References Cited

U.S. PATENT DOCUMENTS

| | | |
|---|---|---|
| 2006/0107486 A1 | 5/2006 | Andre |
| 2007/0012340 A1 | 1/2007 | Jones et al. |
| 2007/0084650 A1 | 4/2007 | Schwei et al. |
| 2007/0272279 A1 | 11/2007 | Foster |
| 2008/0006309 A1 | 1/2008 | Holbrook |
| 2008/0178412 A1 | 7/2008 | Kiter |
| 2008/0210268 A1 | 9/2008 | Metheny et al. |
| 2008/0216879 A1 | 9/2008 | Johnson |
| 2012/0024326 A1 | 2/2012 | McCarthy |
| 2013/0087176 A1 | 4/2013 | Sappington et al. |

\* cited by examiner

CART CLEANING MACHINE

This United States utility patent application claims priority on and the benefit of provisional application 63/117,322 filed Nov. 23, 2020, the entire contents of which are hereby incorporated herein by reference.

BACKGROUND OF THE INVENTION

1. Field of the Invention

The present invention relates to a cart cleaning machine with a dock and a movable gantry.

2. Description of the Related Art

A shopping cart is a staple at many if not most retail establishments. It is customary for the establishments to remove debris from carts as they are returned from the lot and placed in a corral or cart lobby. It is less common, but still customary, for some establishments to hose down the carts periodically with water to remove stuck-on debris. While such an approach may be effective for debris, it is not effective for disinfecting the carts.

Mobile cart cleaners have existed for some time. The basic premise of the mobile cart cleaner is that the carts are removed from the corral (taking the carts offline from the normal handling process) and are fed through the cleaner or alternatively are moved through the cleaner before being placed in the corral.

Other cleaners exist through which the carts pass. Some are large and stationary. Others are small and movable. Yet, in each of the existing machines, none have the unique features of the present invention.

Thus, there exists a need for cart cleaning machine that solves these and other problems.

SUMMARY OF THE INVENTION

A cart cleaning machine has a foundation, a dock, a movable gantry, and a bellow assembly. The foundation has a cart path spanning the length of the foundation between a first end and a second end. Two side channels are also provided. A dock is stationarily mounted to the foundation. The dock has the shape of an inverted U to allow carts to pass through. The dock has a controller, a water inlet, a chemical station, and line management devices. The movable gantry is movable with respect to the foundation. It has a drive mechanism with sprockets that interact with bands spanning between the foundation ends. The gantry has spray nozzles and blow off openings. The bellow assembly is between the dock and the gantry. Water and electric lines pass through the bellow assembly and span between the dock and movable gantry.

According to one advantage of the present invention, the cleaner has a foundation with ramps having flared ends. The flared ends advantageously allow the carts to be directed onto a frame path for cleaning.

According to another advantage of the present invention, a dock is provided at a stationary location with respect to the foundation. The dock is according a fixed base station. The dock has a chemical station and a water and electrical hookup. The dock can be located at a desirable location in the cart corral. Also, the chemical station and water hookup are reversible within the dock allowing for preferred orientation (left/right side) of these components per the location of the cleaner in the corral in relation to adjacent cleaning units, walls and/or operator preference.

According to a further advantage of the present invention, a movable gantry is provided. The movable gantry contains spray nozzles and a blower assembly. The gantry moves away from and retract towards the dock during the cleaning process.

Advantageously, the spray nozzles can be quick connect nozzles for easy and fast interchangeability.

Also advantageously, the blower assembly is operable during the spray phase to increase turbulence and accordingly coverage, as well as during the blow off phase to remove liquid from the carts.

According to a still further advantage of the present invention, the length of the cleaner is modular. In one embodiment, one or more sections of foundation can be modularly connected with a dock at one of the foundation and wherein the gantry is movable to and from the opposite end of the foundation. In another embodiment, the dock is in the middle of the foundation and two gantries move in opposite direction relative to the foundation to and from opposite foundation ends.

According to a still further advantage yet of the present invention, the cleaner has two drive guides and two bands that span between ramps at opposite ends of the frame. The bands each preferably have ridges on the underside thereof and wrap upwards from two gantry wheels and over a sprocket. The gantry has a movement mechanism with two sprockets which are connected with a drive shaft. Rotation of the drive shaft causes the sprockets to interface with the bands to move the gantry selectively in either direction to extend and retract the gantry relative to the dock upon the foundation.

According to a still further advantage yet of the present invention, each gantry wheel has outer flanges that straddle respective belts to maintain proper orientation of the gantry with respect to the belts.

According to a still further advantage yet of the present invention, the gantry speed and rate of liquid dispersion can be selected by the user. This is advantageous as some cart types such as wire carts are easier to cover and other cart types such as plastic carts are more challenging to cover. It is desirable to use only as much liquid and chemicals as necessary to cover the carts for cleaning as it reduces waste and reduces the required liquid management.

According to a further advantage yet of the present invention, blowers remove excess fluid from the carts.

According to a still further advantage yet of the present invention, a bellow assembly is provided to cover the carts while the gantry is extended with respect to the dock. The bellow assembly has several advantages.

The bellow assembly contains spray to within the cleaner. This reduces unnecessary chemical exposure to nearby people and objects. It also prevents the overspray from creating slippery conditions within the cart corral.

The bellow assembly is highly compact when retracted yet able to be extended to a considerable length. In one embodiment, the bellow assembly can be extended from 20 inches to 20 feet.

When the bellow assembly is retracted, it allows for easy access and complete view of processed carts. It also minimizes required space as access to carts is increased. Unobstructed access to carts also allows for greater airflow around the carts encouraging evaporation of any remaining liquid.

The bellow assembly further have stiffeners that enhance the rigidity of the bellow, that support liquid and electric lines between the dock and the gantry, and that support bellow wheel supports that support guide wheels.

According to a still further advantage yet of the present invention, the dock has an electric line recoiler and a liquid line recoiler. The recoilers operate as the gantry is being extended and retracted to manage the respective lines by eliminating slack by placing the respective lines in tension as the gantry is being extended.

According to a still further advantage yet of the present invention, the foundation has shaker breaks that the carts must pass over. The shaker breaks cause the carts to bounce slightly as they are moved over the breaks, thereby causing excess fluid to drop from the carts.

According to a still further advantage yet of the present invention, absorbent runners are provided under cart supporting grates. The pads absorb excess fluid and can be replaced as necessary.

According to a still further advantage yet of the present invention, the cleaner is designed to operate under municipal water pressure. A booster pump can be used when required if the existing water pressure is insufficient.

According to a still further advantage yet of the present invention, the cleaner is modular in length (number of carts in a row) and width (how many rows can be processed with the cleaner).

According to a still further advantage yet of the present invention, the cleaner can be used in both pass-through and closed-ended (dead end) corrals.

According to a still further advantage yet of the present invention, the chemical station can have a sensor, such as a float sensor, that senses when there is insufficient chemicals available for use whereby the cleaner can be rendered inoperable until chemicals are added.

According to a still further advantage yet of the present invention, the cleaner has rails. The rails can prevent contact between a foreign object and the bellow assembly. The rails also can prevent people from inadvertently stepping onto the cleaner.

Other advantages, benefits, and features of the present invention will become apparent to those skilled in the art upon reading the detailed description of the invention and studying the drawings.

DETAILED DESCRIPTION OF PREFERRED EMBODIMENTS

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

The present invention is useful for cleaning carts 5. Carts 5 come in many shapes, sizes and configurations. Some are made of wire and are relatively easy to clean while others are made of plastic with recessed areas that are more challenging to clean.

Figure 1:
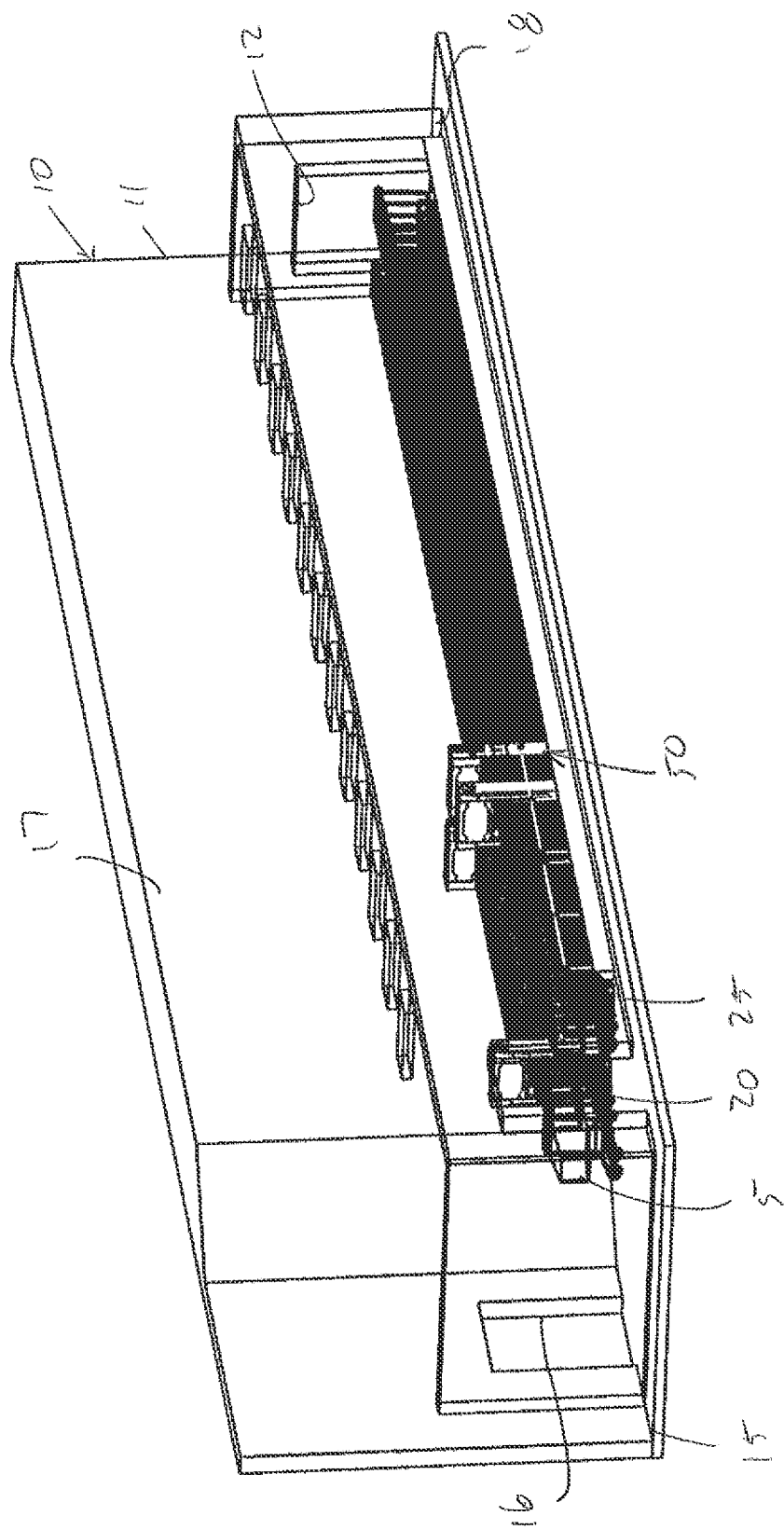
FIG. 1 is a perspective view of a cart corral with two units of a preferred embodiment of the present invention.
Figure 2:
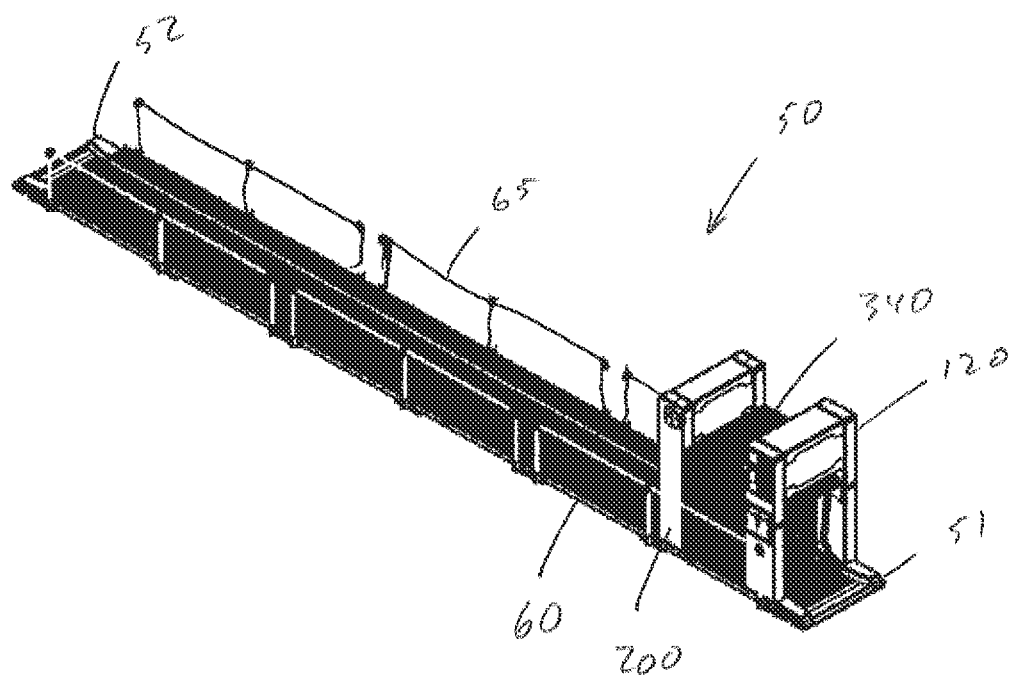
FIG. 2 is a perspective view of the embodiment illustrated in FIG. 1.
Figure 3:
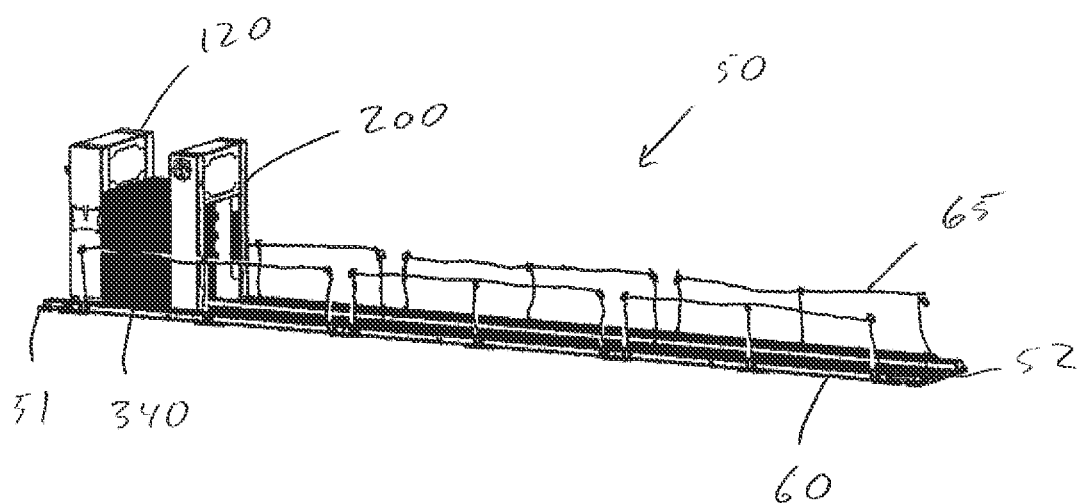
FIG. 3 is a reverse perspective view of the embodiment illustrated in FIG. 2.
Figure 4:
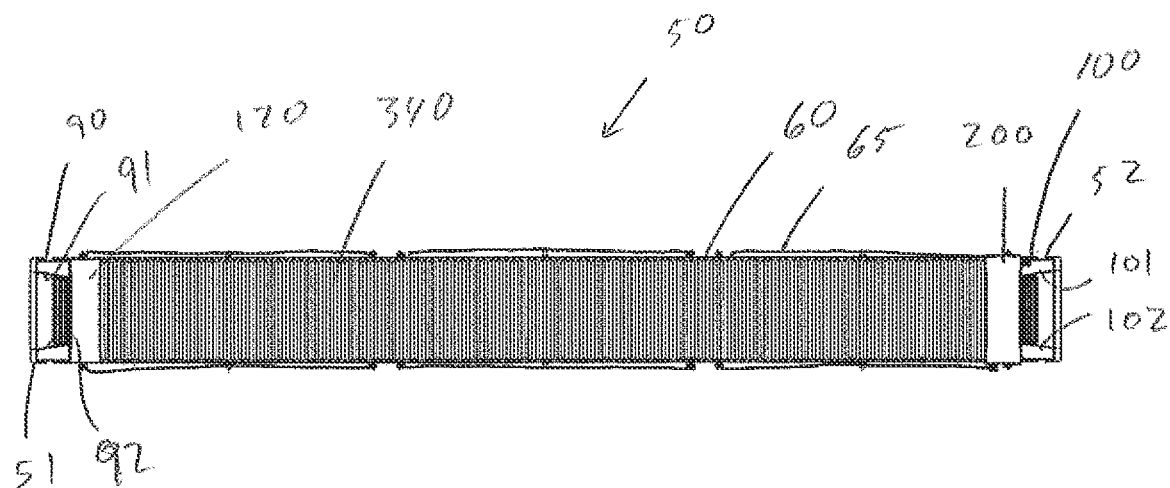
FIG. 4 is a top view of the embodiment illustrated in FIG. 2.
Figure 5:
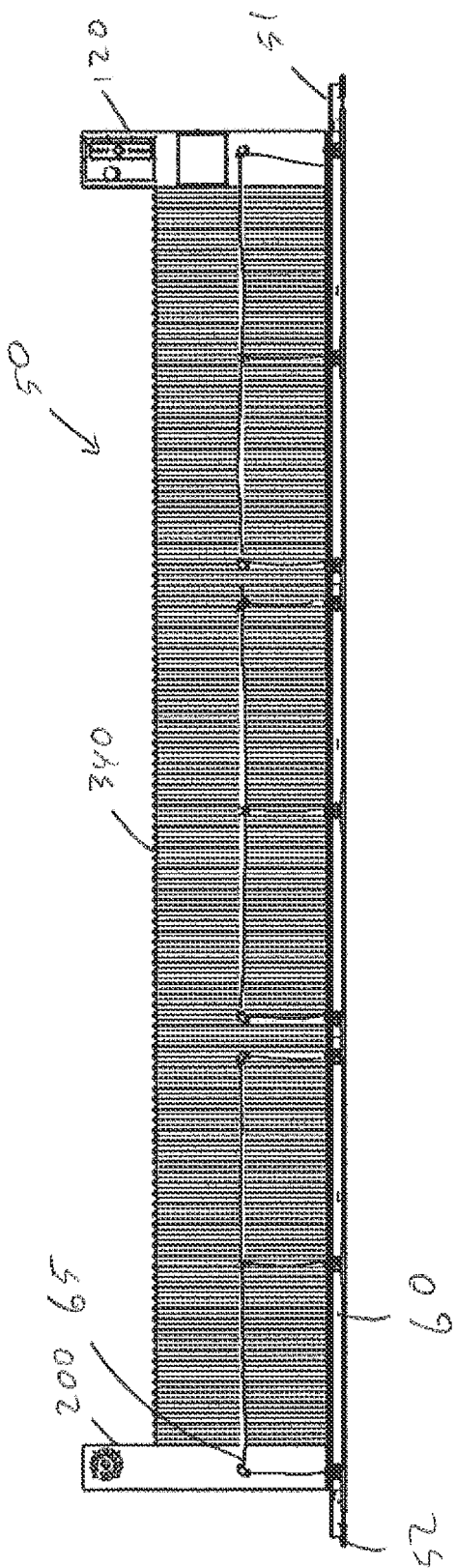
FIG. 5 is a side view of the embodiment illustrated in FIG. 2.
Figure 6:
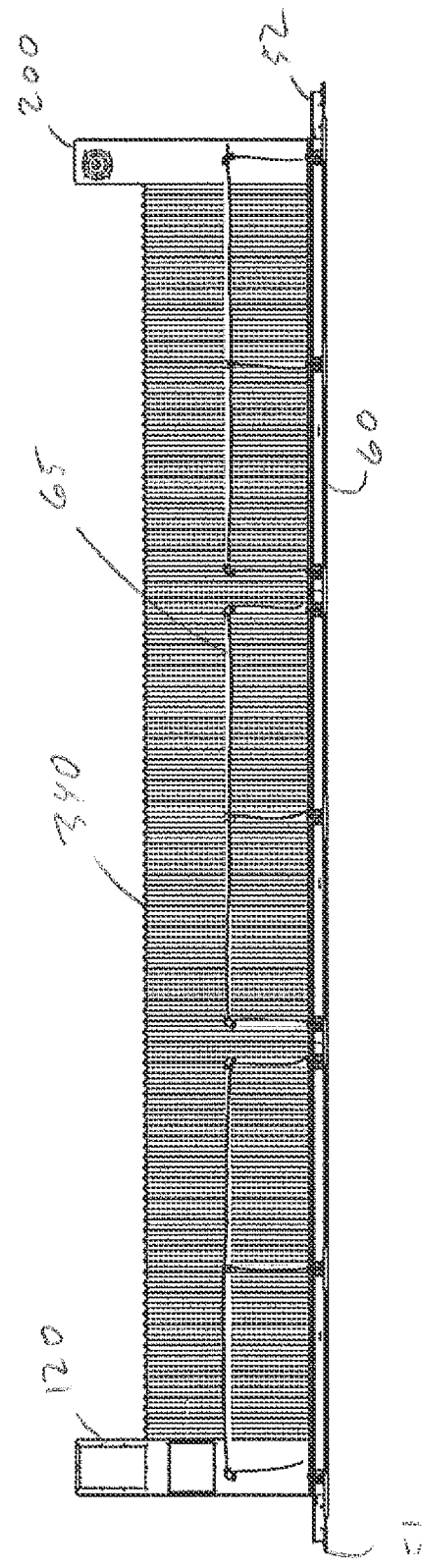
FIG. 6 is a reverse side view of the embodiment illustrated in FIG. 2.
Figure 7:
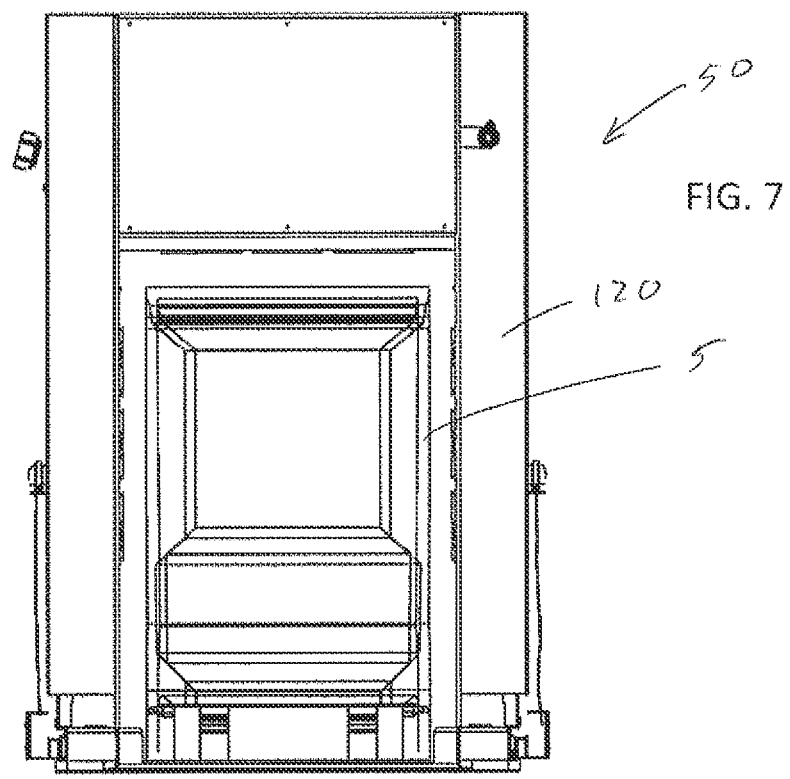
FIG. 7 is an end view of the embodiment illustrated in FIG. 2 shown with a cart in the cleaner.
Figure 8:
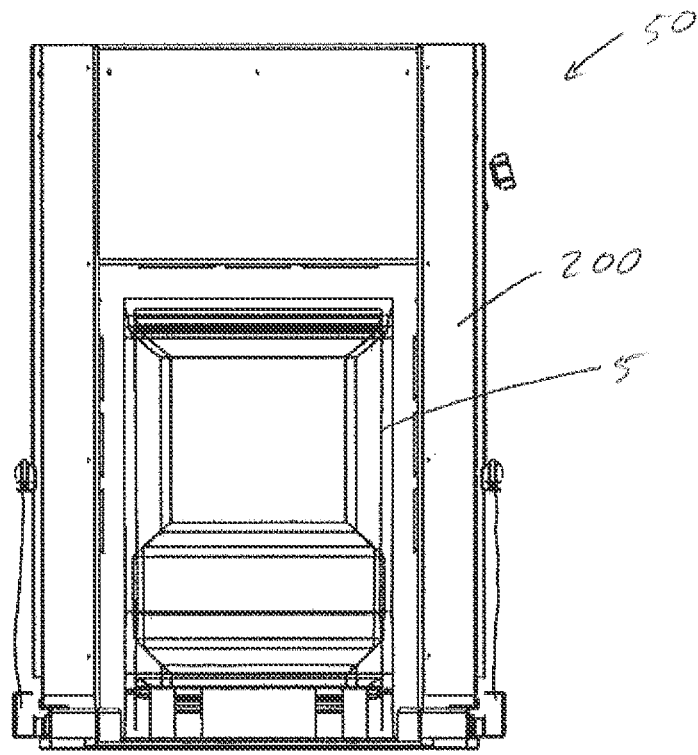
FIG. 8 is a reverse end view of the embodiment illustrated in FIG. 2 shown with a cart in the cleaner.
Figure 9:
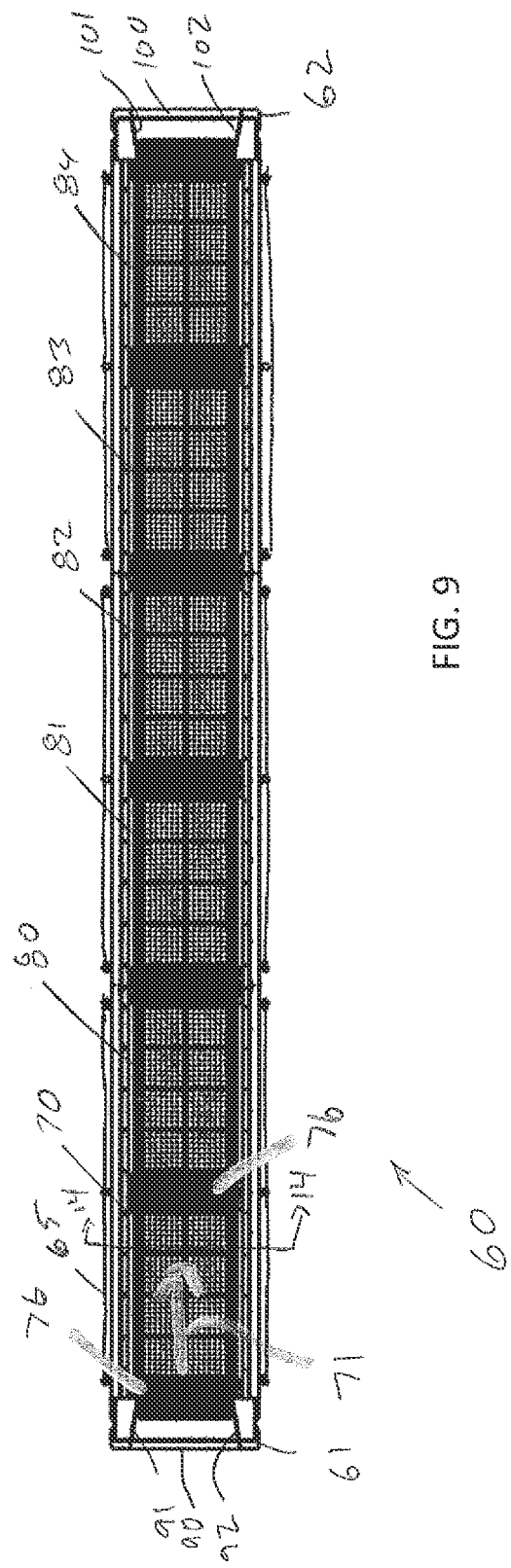
FIG. 9 is a top isolation view of a preferred embodiment of a foundation of the present invention.
Figure 10:
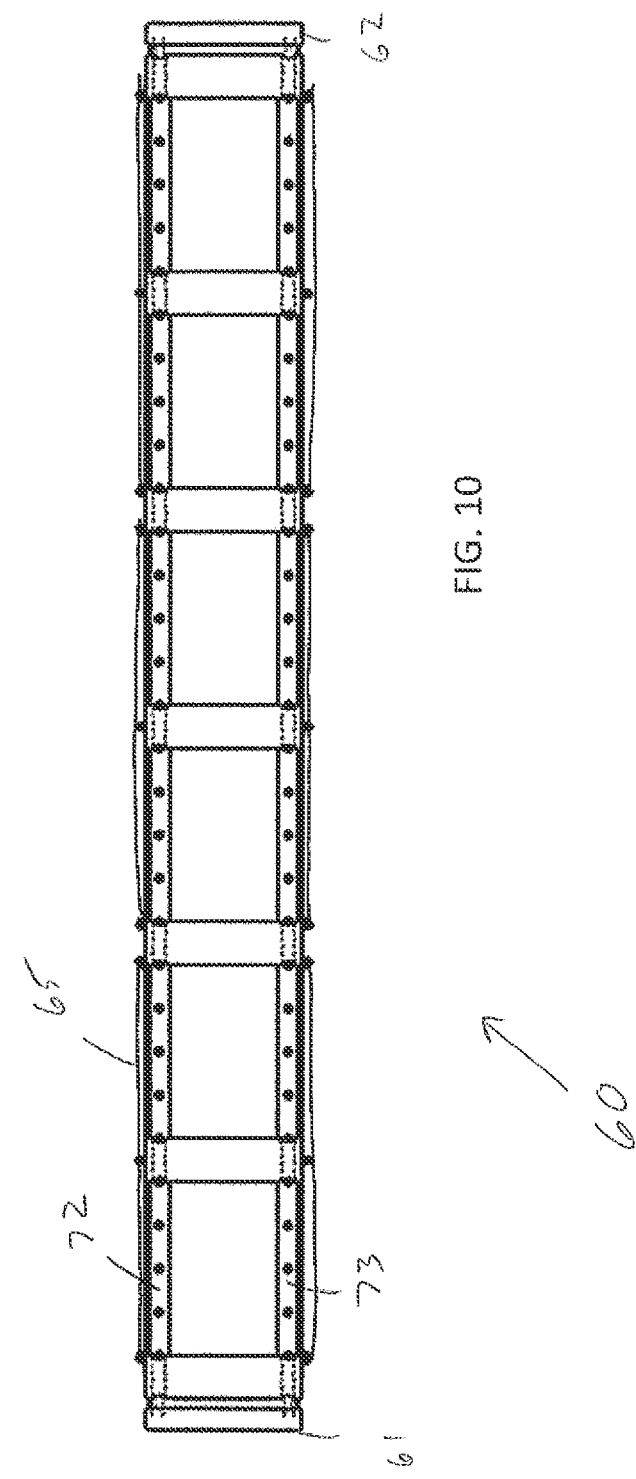
FIG. 10 is a bottom view of the foundation illustrated in FIG. 9
Figure 11:
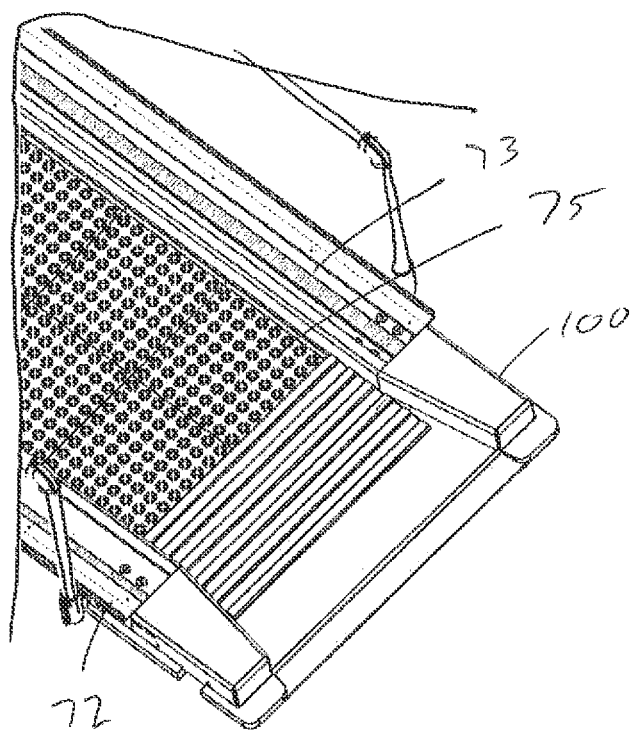
FIG. 11 is a partial perspective end view of the foundation illustrated in FIG. 9.
Figure 12:
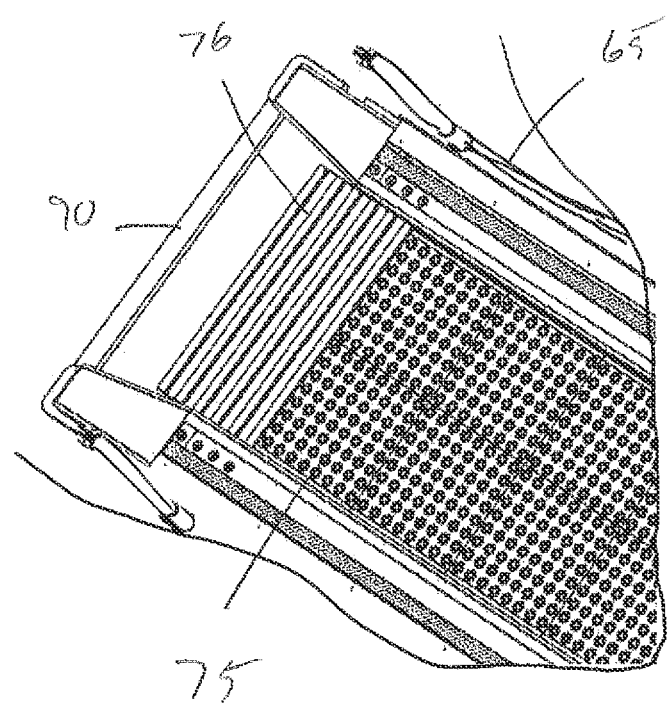
FIG. 12 is a partial perspective end view of a second end of the foundation illustrated in FIG. 9.
Figure 13:
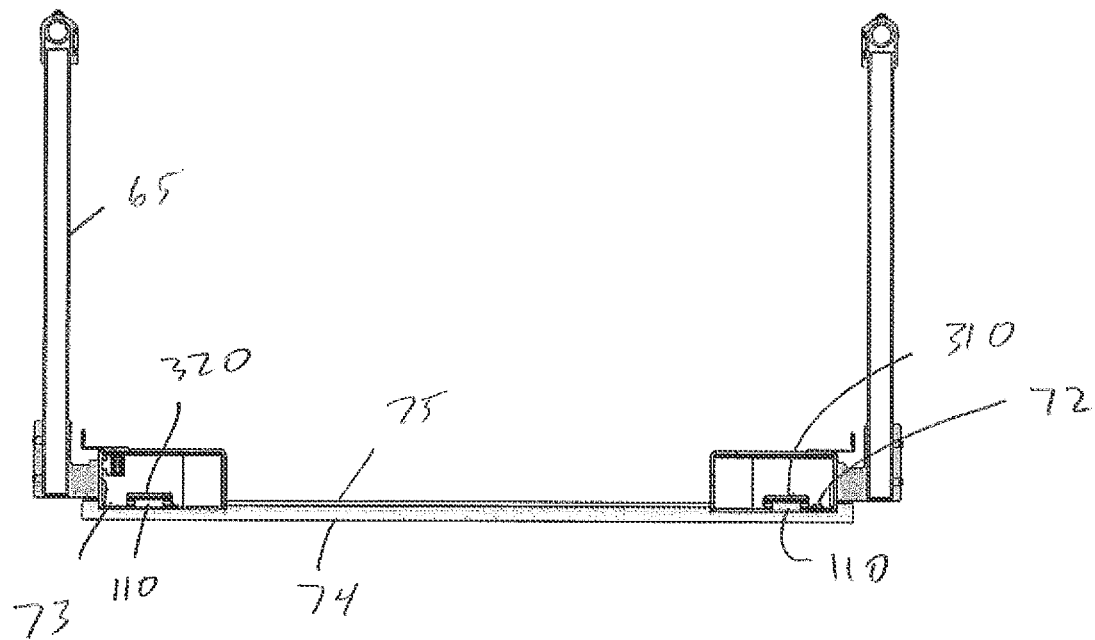
FIG. 13 is an end view of the foundation illustrated in FIG. 9.

Carts 5 are typically stored in a corral 10 such as the one illustrated in FIG. 1. The corral 10 has one end 11 with a cart entrance 12 and an opposed end 15 with a cart exit 16. The corral 10 has sides 17 and 18, respectively. Rows of carts, for example rows 20 and 25 are longitudinally aligned between sides 17 and 18. It is appreciated that two rows of carts are shown for illustration purposes only and that greater or fewer numbers of rows could be used without departing from the broad aspects of the present invention. Each row of carts is preferably cleaned with a cleaner 50.

A preferred embodiment of a cleaner 50 is illustrated in FIGS. 2-8. Cleaner 50 has a first end 51 and a second end 52. The cleaner 50 preferably has a foundation 60, a dock 120, a gantry 200 and a bellow assembly 340. Each of these components are described in detail below.

Figure 14:
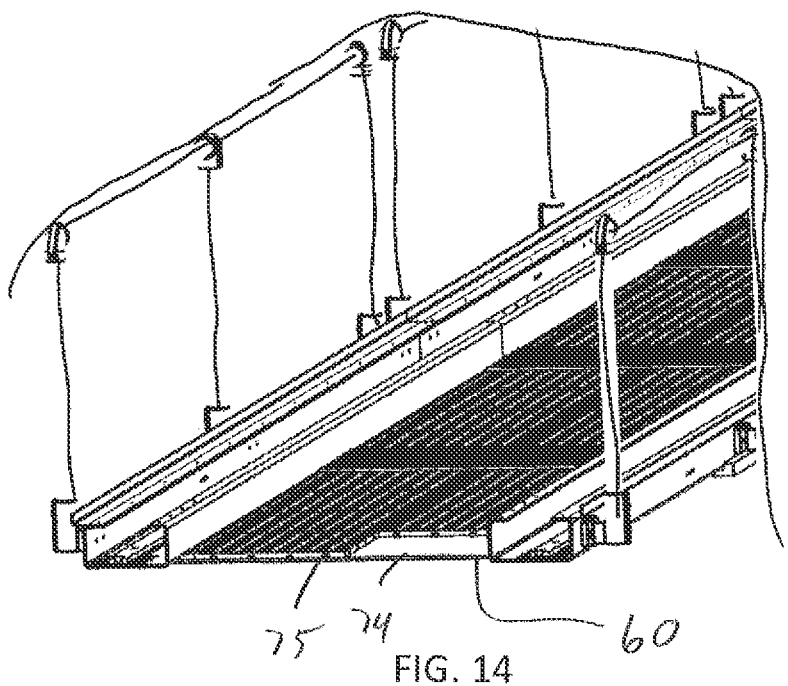
FIG. 14 is a perspective sectional view taken along line 14-14 in FIG. 9.
Figure 15:
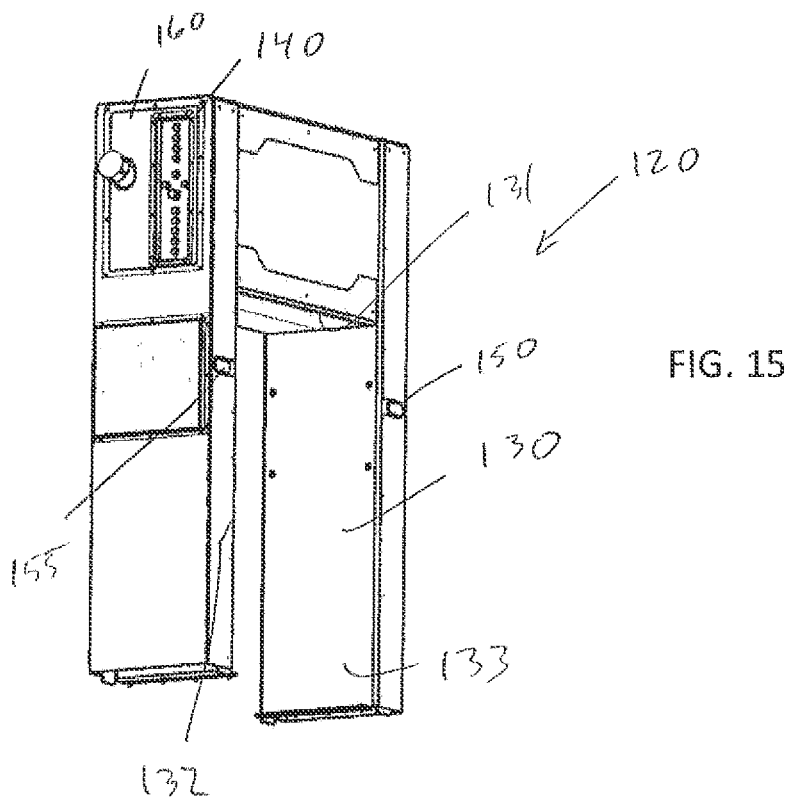
FIG. 15 is a perspective view of a preferred embodiment of a dock of the present invention.
Figure 16:
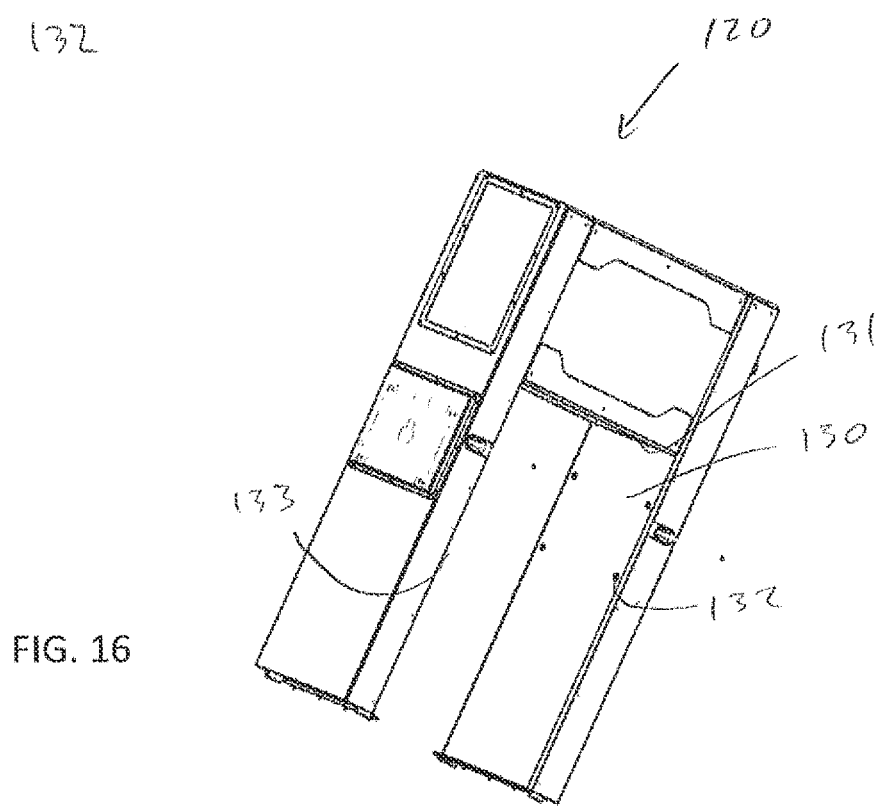
FIG. 16 is a reverse perspective view of the dock illustrated in FIG. 15.
Figure 17:
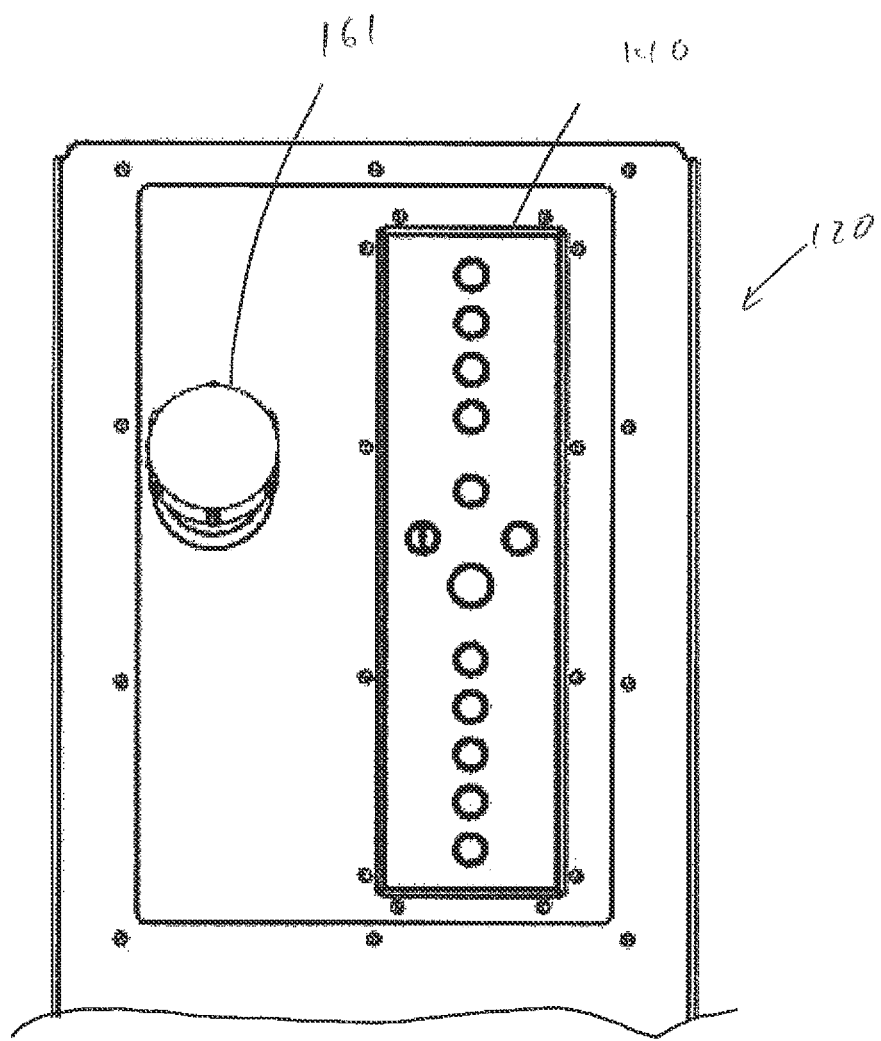
FIG. 17 is a partial close-up view of a controller face of the dock illustrated in FIG. 15.
Figure 18:
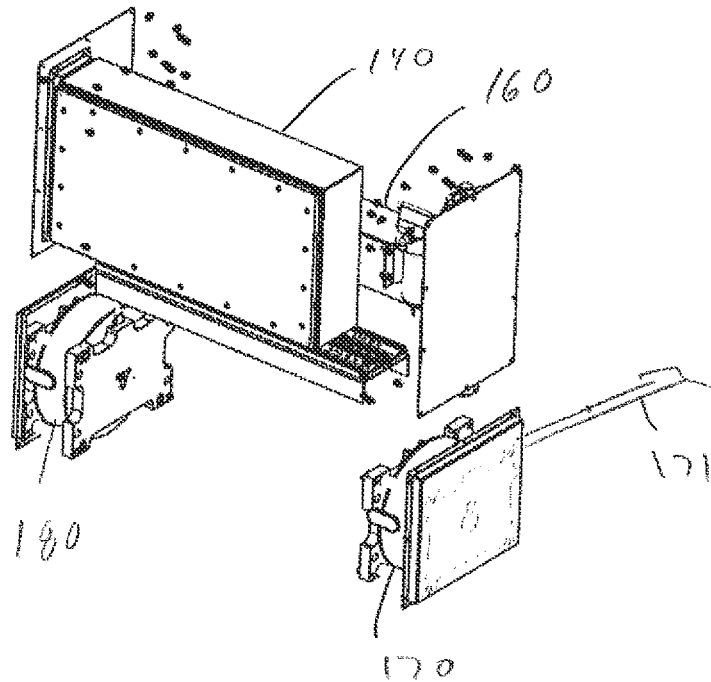
FIG. 18 is an isolation perspective view of a controller, a water inlet, a chemical station and two recoilers of the dock.
Figure 19:
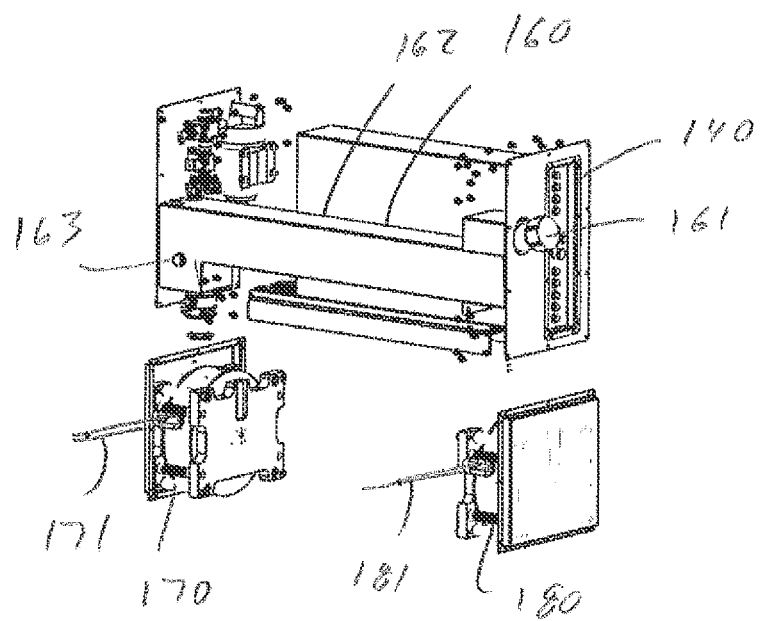
FIG. 19 is a reverse perspective view of the components illustrated in FIG. 18.
Figure 20:
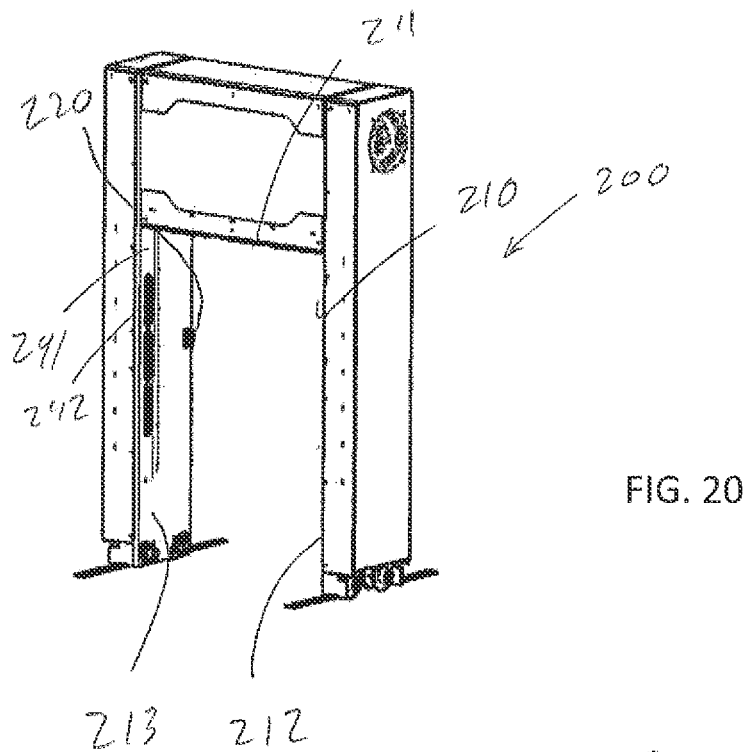
FIG. 20 is a perspective view of a preferred embodiment of a gantry of the present invention.
Figure 21:
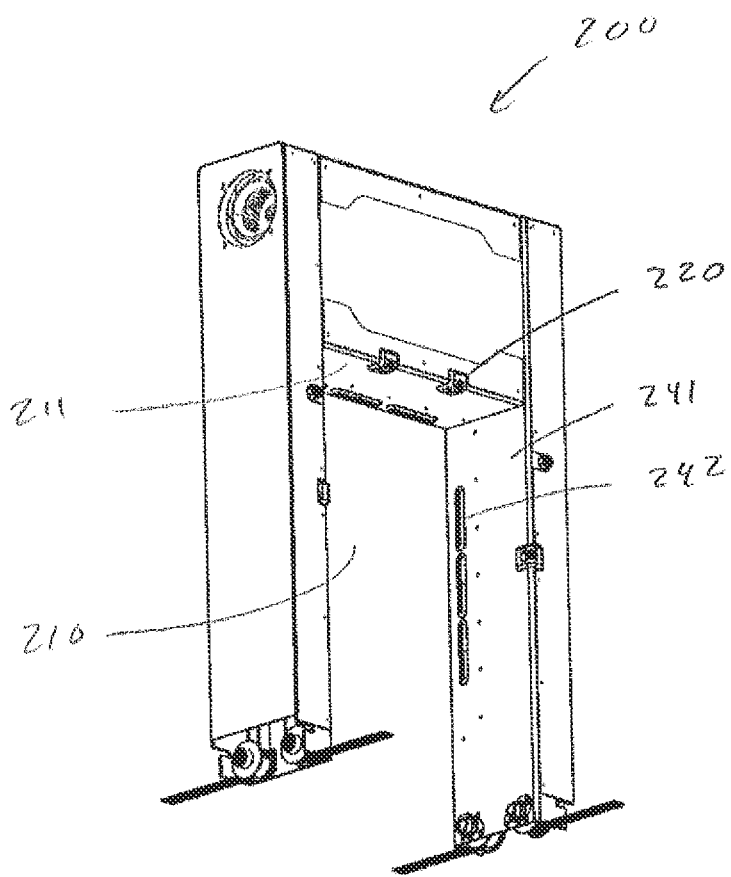
FIG. 21 is a reverse perspective view of the gantry illustrated in FIG. 20.
Figure 22:
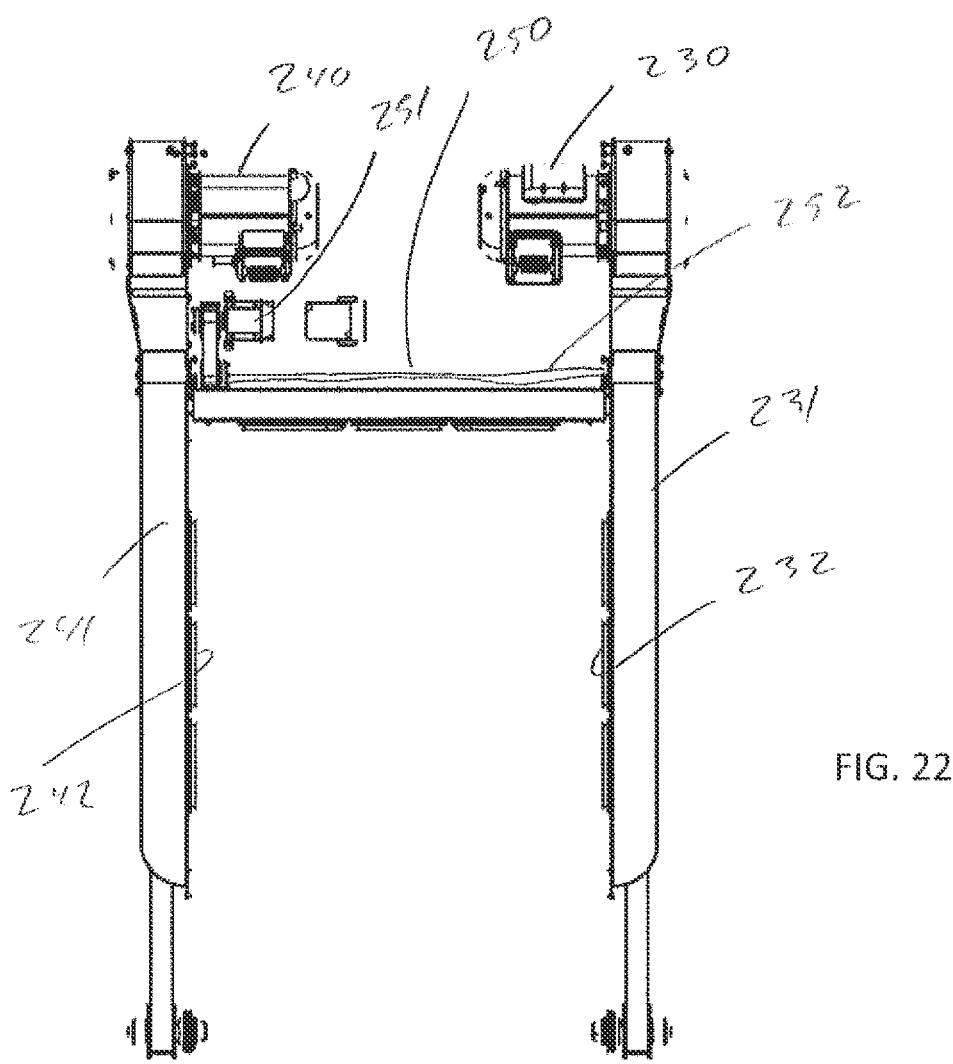
FIG. 22 is an end view of blowers, ducting, blowing openings and movement mechanism of the gantry.
Figure 23:
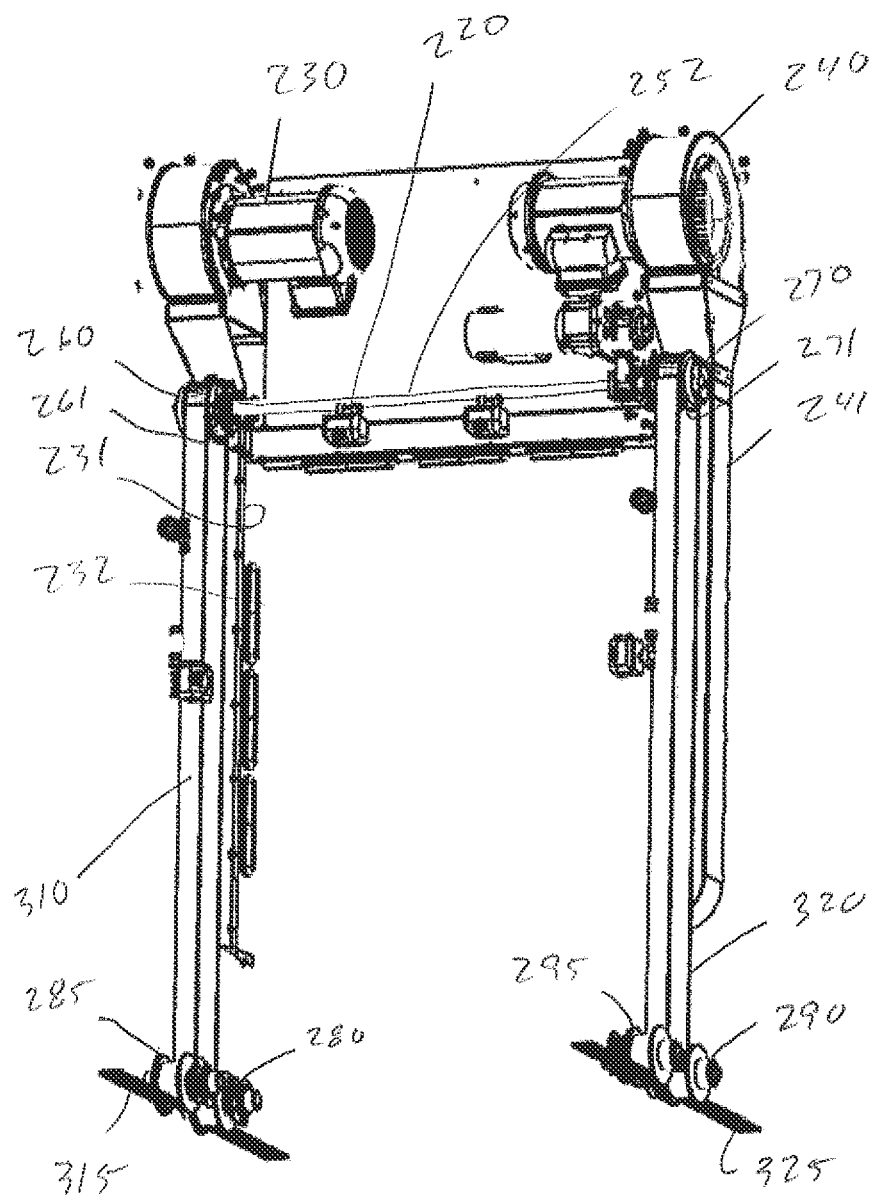
FIG. 23 is a perspective view of blowers, ducting, blowing openings, nozzles and movement mechanism of the gantry.
Figure 24:
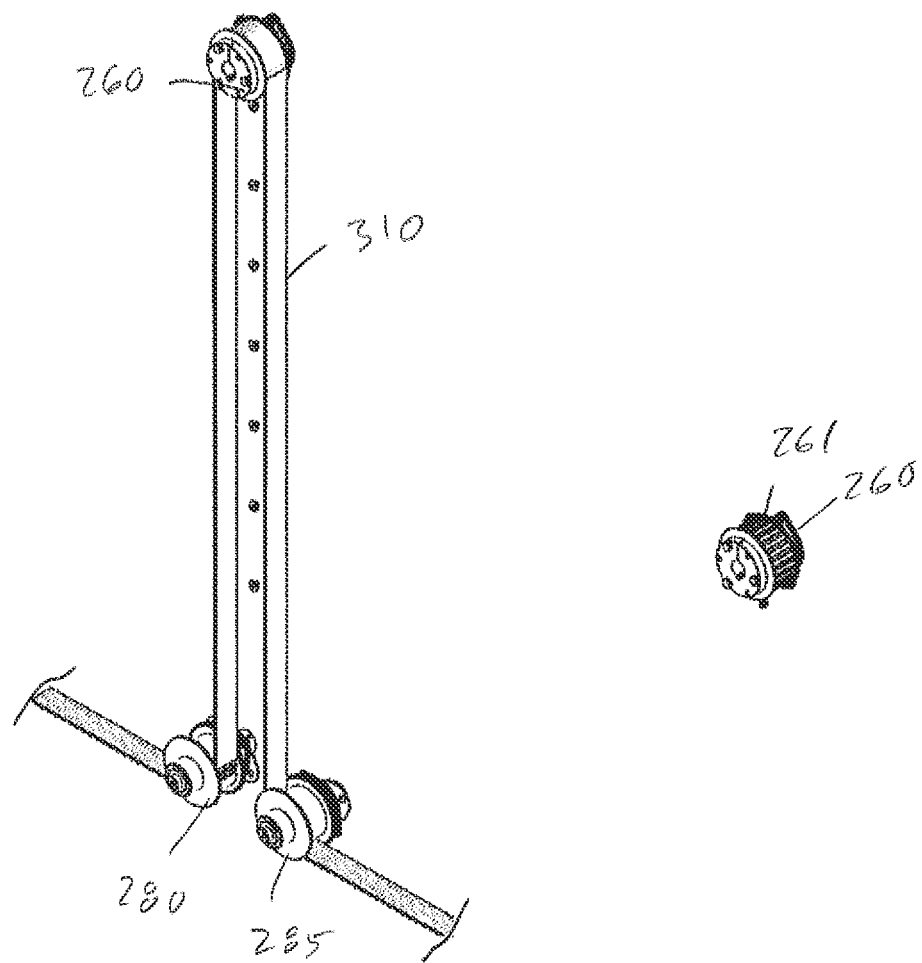
FIG. 24 is a partial side view showing the belt, gantry wheels and gantry sprocket of the present invention.
Figure 25:
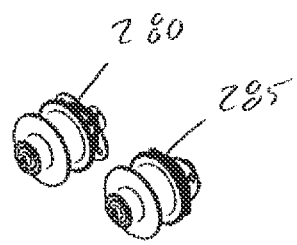
FIG. 25 is an isolation perspective view of gantry wheels and a sprocket.
Figure 26:
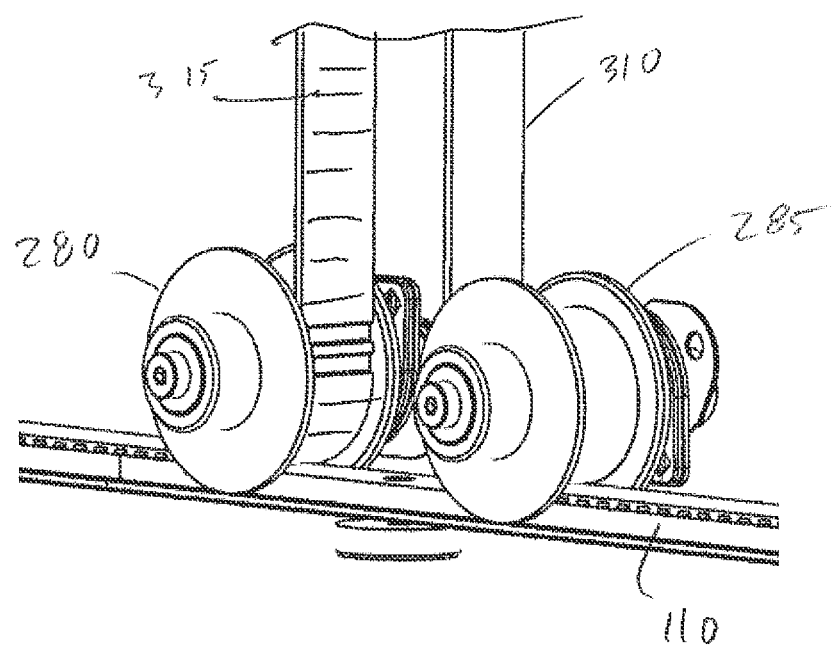
FIG. 26 is a partial perspective view showing gantry guide wheels, a band and a drive guide.
Figure 27:
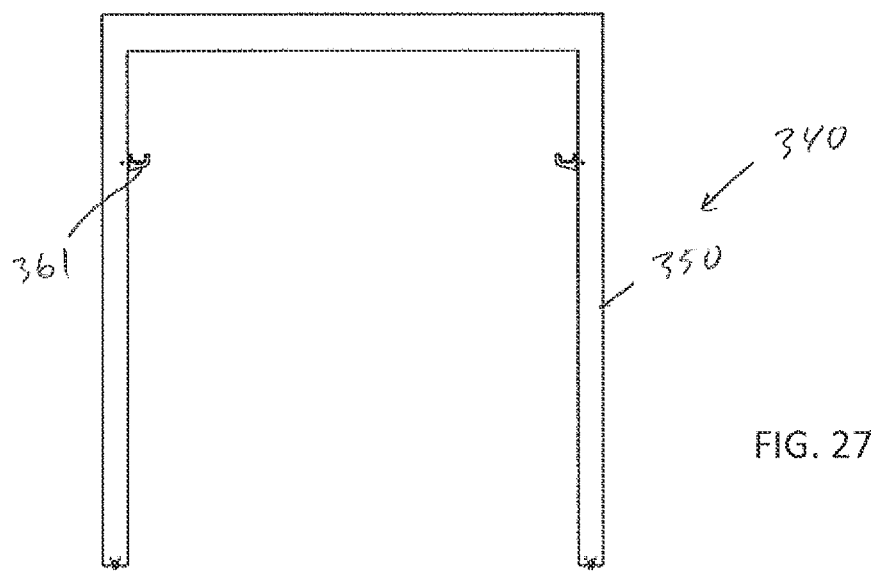
FIG. 27 is an end view showing a preferred embodiment of the bellow assembly of the present invention.

A preferred embodiment of a foundation 60 is illustrated in FIGS. 9-14. Foundation 60 has opposed ends 61 and 62. Exterior rails 65 are provided longitudinally between the ends 61 and 62. The foundation 60 has at least one frame 70 (or modular frame or modular frame segment) with a path 71 that is centrally located and longitudinally oriented. Side channels 72 and 73, respectively, are provided. An absorbent runner 74 can be placed with the path 71 and is covered with a grate or several grates 75. One grate 75 is shown removed in FIG. 14 showing the runner 74. Each frame has a shaker break 76 at each end of the frame 70. The shaker breaks 76 are a series of tabs that carts 5 move over. The carts shake as they travel over the breaks 76 to promote any liquid drops to fall from the carts. The absorbent runners 74 can be changes as needed. The foundation 60 is modular in length. In the illustrated embodiment, the foundation has frames 70, 80, 81, 82, 83 and 84, each connected end to end in a single row. It is appreciated that there could be more or fewer frame sections without departing from the broad aspects of the present invention. Each frame section is preferably similar and results in a single continuous cart path from end 61 to end 62 of the foundation 60.

A ramp 90 having two flares 91 and 92 is provided at one end 61 of the foundation 60. A second ramp 100 having two flares 101 and 102 is provided at the other end 62 of the foundation. The flares direct the carts onto the cart path.

A drive guide 110 with runs along each side channel 72 and 73 of the frame (and all frames) from end to end of the cleaner 50. The drive guides 110 are preferably rigid and linearly oriented.

Turning now to FIGS. 15-19, it is seen that a preferred embodiment of a dock 120 is illustrated. The dock 120 is a fixed base station that is preferably stationary relative to the foundation. The base or dock 120 has a cart opening 130 with a top 131 and two sides 132 and 133. Carts 5 pass through the cart opening when being loaded in the cleaner 50. A controller 140 is provided. The controller 140 is preferably located on a side of the dock 120. It is understood that it can be located elsewhere without departing from the broad aspects of the present invention. A water inlet 150 is also provided. The water inlet 150 is preferably used to hook up to a municipal or other pressurized water source. An electrical inlet 155 is also provided. A chemical station 160 with an inlet 161 and a receptacle 162 is further provided. A user can introduce a quantity, preferably sufficient for many cleaner cycles, of chemicals into the receptacle 162. A sensor 163, such as a float sensor, is provided to sense when the chemical level is insufficient for another cycle, so that the cleaner 50 can be rendered inoperable until more chemicals are added. A recoiler 170 is provided for use with a liquid line 171. The line 171 is extended during operation (as discussed below) and the recoiler maintains a tension on the line and winds the line as the line 171 is being retracted. A recoiler 180 is provided for use with an electric line 181. The line 181 is extended during operation (as discussed below) and the recoiler maintains a tension on the line and winds the line as the line 181 is being retracted. More than one recoiler and associated line may be used for either or both of liquid and power distribution. Water introduced through the water inlet and chemicals from the receptacle 162 are mixed before being introduced into liquid line 171. The electric line 181 is electrically connected to a power source.

The dock 120 is preferably secured in a fixed location relative to the foundation 60. In the embodiment illustrated in FIGS. 2-8, the dock 120 is located at an end of the foundation 60.

Turning now to FIGS. 20-26, it is seen that a gantry 200 is illustrated. The gantry 200 is a movable gantry. The gantry 200 has a cart opening 210 with a top 211 and sides 212 and 213. The cart opening is large enough to allow carts to pass through. Spray nozzles 220 are provided for selectably spraying liquid at selected times. The nozzles are preferably quick-change nozzles. The nozzles are fluidically connected to the liquid line 171. A blower 230 is provided for moving air through ducting 231 and out through openings 232. A second blower 240 is also provided for moving air through ducting 241 and out through openings 242. It is appreciated that there could be more or less than two blowers without departing from the broad aspects of the present invention. The blower openings are at the forward end of gantry 200 (forward end when advancing) and the nozzles are at the trailing end of the gantry 200. It is appreciated that the orientation of these components may be reversed depending upon conditions of use or other factors.

The gantry 200 further has a movement mechanism 250. The movement mechanism 250 has a motor 251 operable to turn a shaft 252. The shaft 252 is preferably laterally oriented between sides of the gantry 200 above the cart opening 210. A sprocket 260 with cogs 261 is at one end of the shaft 252. A sprocket 270 with cogs 271 is at the opposite end of the shaft 252. The sprockets 260 and 270 rotate in tandem with the shaft 252. Two lower wheels 280 and 285 are on one side of the gantry and two wheels 290 and 295 are on the opposite side of the gantry. Each wheel has two outer rims or flanges. The rims can be weight bearing components. The wheels are not driven wheels and accordingly act as rollers for the gantry to move upon relative to the foundation 60.

A band 310 with ridges 315 on the underside thereof is provided. The band 310 is preferably a flexible band. The band 310 has a first end stationarily connected to end 61 of the foundation 60. The band 310 has a second end stationarily connected to end 62 of the foundation 60. The top side of band 310 passes beneath wheels 280 and 285 between the wheel rims. The band loops up between wheels 280 and 285 and over sprocket 260. The ridges 315 on the underside of the band 310 mate with the cogs 261 of sprocket 260. In this regard, rotation of the shaft, and accordingly the sprocket 260 causes the gantry to move relative to the band 310 and hence relative to the foundation 60.

A second band, band 320, with ridges 325 on the underside thereof is provided. The band 320 is preferably a flexible band. The band 320 has a first end stationarily connected to end 61 of the foundation 60. The band 320 has a second end stationarily connected to end 62 of the foundation 60. The top side of band 320 passes beneath wheels 290 and 295 between the wheel rims. The band loops up between wheels 290 and 295 and over sprocket 270. The ridges 325 on the underside of the band 320 mate with the cogs 271 of sprocket 270. In this regard, rotation of the shaft, and accordingly the sprocket 270 causes the gantry to move relative to the band 320 and hence relative to the foundation 60.

Bands 310 and 320 are on opposite sides of the foundation 60. Each band preferably rests atop a drive guide 110.

It is appreciated that since the sprockets 260 and 270 rotate in tandem, that the gantry moves in a straight line upon the foundation 60.

Figure 28:
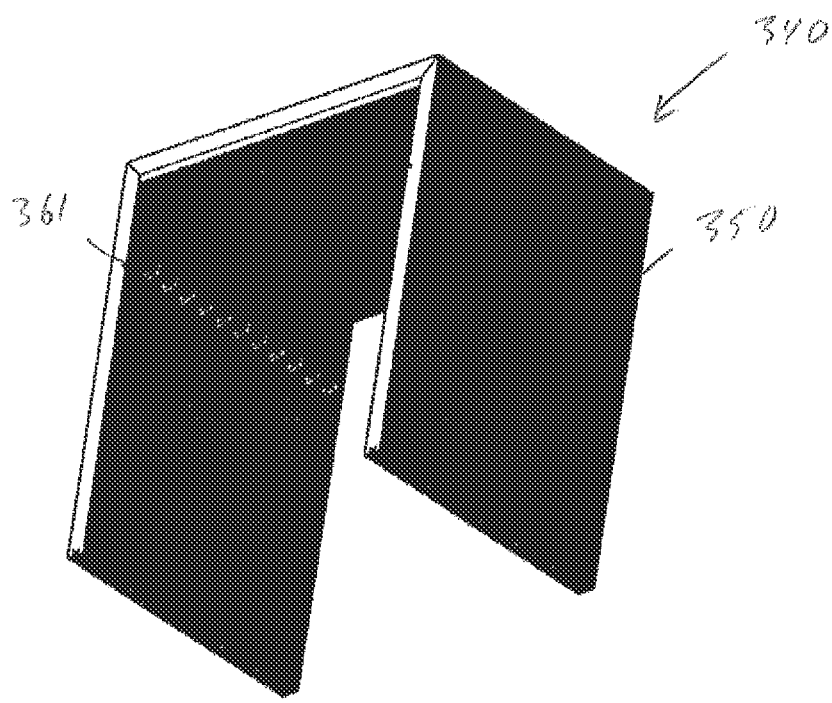
FIG. 28 is a perspective view showing the bellow assembly in a retracted position.
Figure 29:
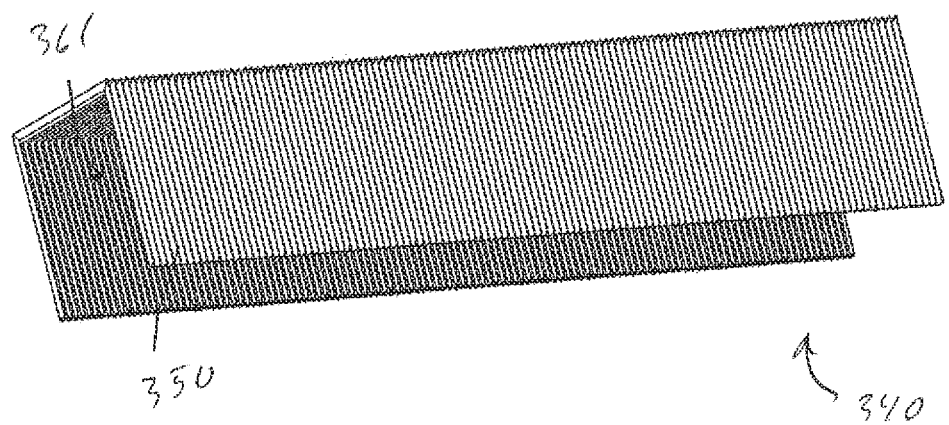
FIG. 29 is a perspective view showing the bellow assembly in an extended position.
Figure 30:
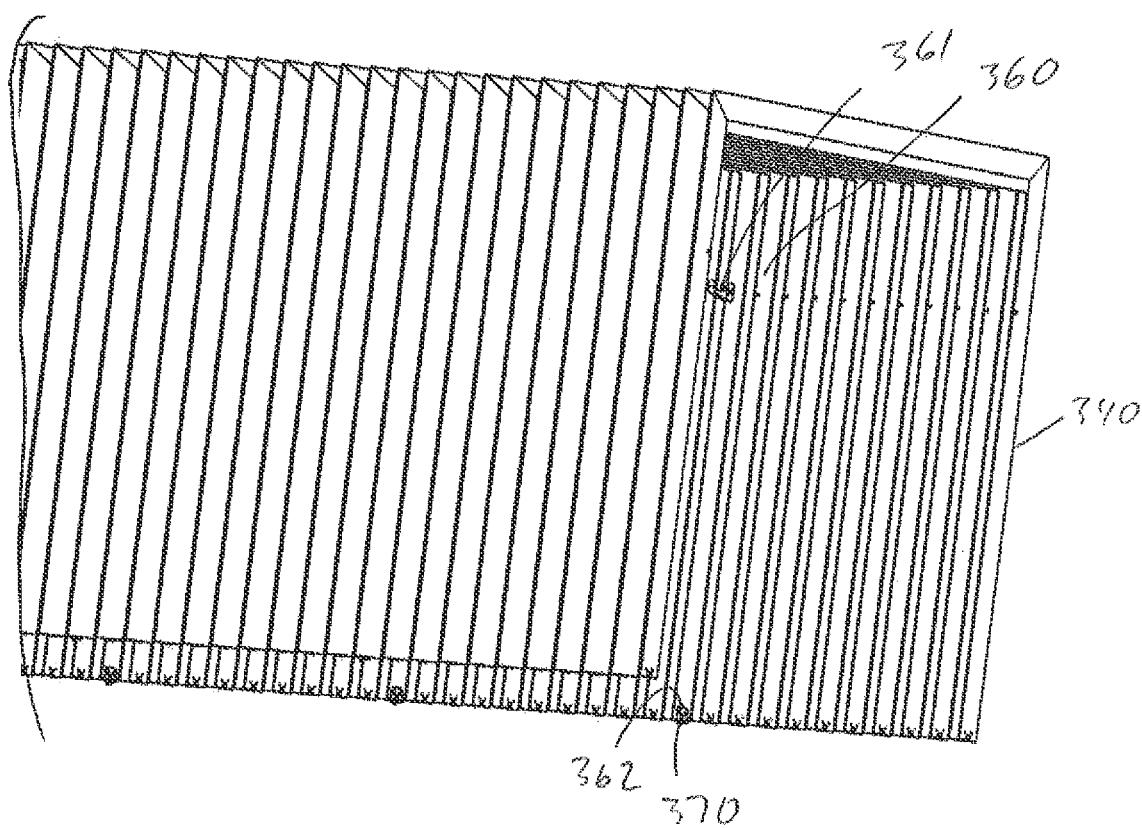
FIG. 30 is a lower perspective view showing an end of the bellow assembly in an extended position.
Figure 31:
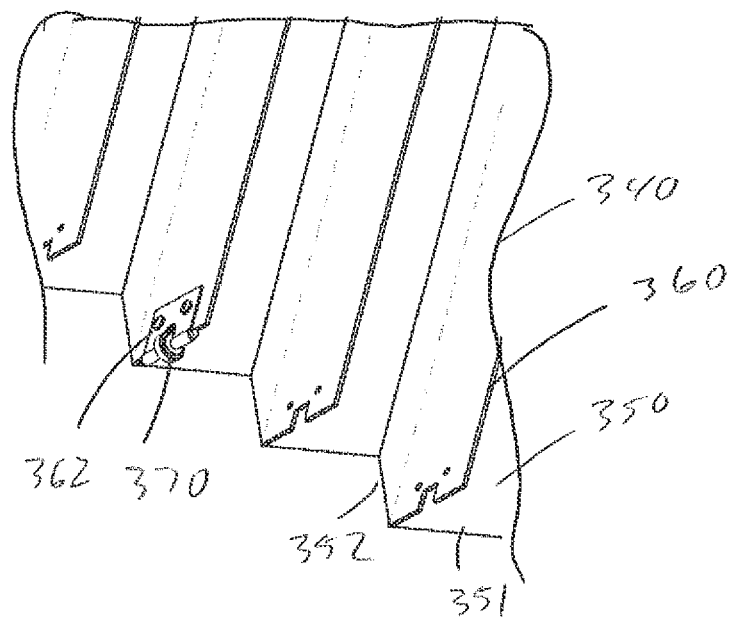
FIG. 31 is a partial perspective view showing a wheel support and bellow assembly guide wheel.
Figure 32:
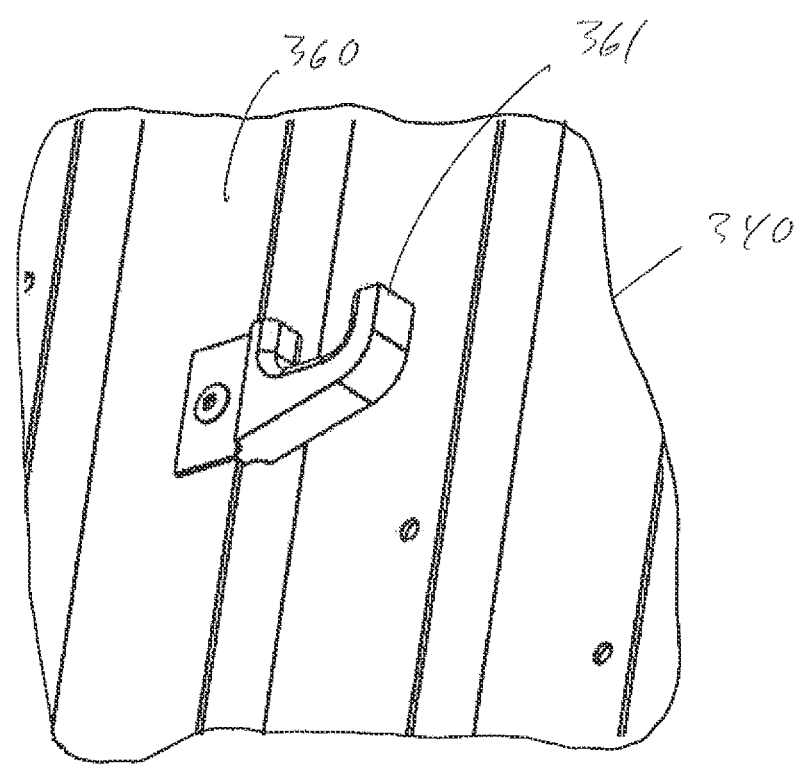
FIG. 32 is a partial perspective view showing a line hanger.

Turning now to FIGS. 27-32, it is seen that a preferred embodiment of a bellow assembly 340 is illustrated. The bellow assembly 340 has a shell 350 with an accordion style structure having alternating oriented faces 351 and 352, respectively. The alternating face pattern is repeated along the bellow assembly longitudinal axis a sufficient number of times to accommodate an overall selected extended length. Stiffeners 360 are provided. Each stiffener 360 is a rigid piece of material that is oriented generally perpendicular to the longitudinal axis of the bellow assembly 340. Several stiffeners 360 have hangers 361 on vertical stiffener sections, and also a wheel supports 362 at lower ends of the respective stiffeners. The hangers 361 support liquid line 171 and electric line 181 as they pass through the bellow assembly 340. The wheel supports 361 support bellow assembly guide wheels 370. The bellow assembly can be in a fully retracted position as seen in FIG. 28, a fully extended position as seen in FIG. 29 or any intermediate position there between. In a fully extended position, the bellow assembly 340 covers or fully encapsulates the carts that are being processed in the batch.

The bellow assembly 340 is connected to the dock 120 at one end and to the gantry 200 at the opposite end. Movement of the gantry 200 relative to the dock 120 causes the bellow assembly 340 to extend and retract in tandem with the gantry movement.

The guide rails 65 protect the bellow assembly 340 by preventing lateral contact between a foreign object and the side of the bellow assembly 340.

Workflow of the present invention is illustrated in FIGS. 33-48. It is noteworthy that the foundation in FIGS. 33-48 is shown with an optional center island segregating the cart path into two distinct paths.

Figure 33:
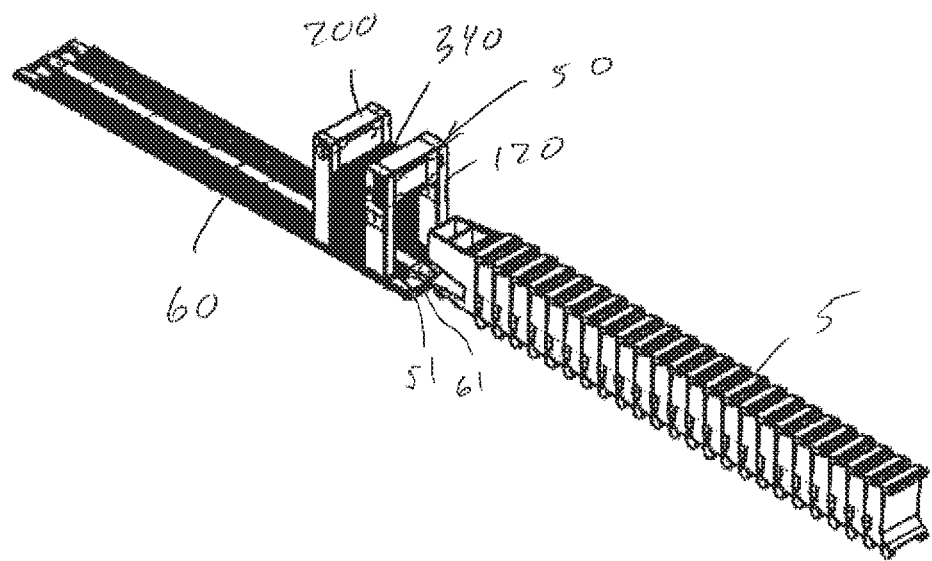
FIG. 33 is a perspective view showing carts lined up to be processed.

In FIG. 33, an elongated row of carts is lined up behind the cleaner end 51. It is seen that there can be more then enough carts lined up for more than one batch of processing.

Figure 34:
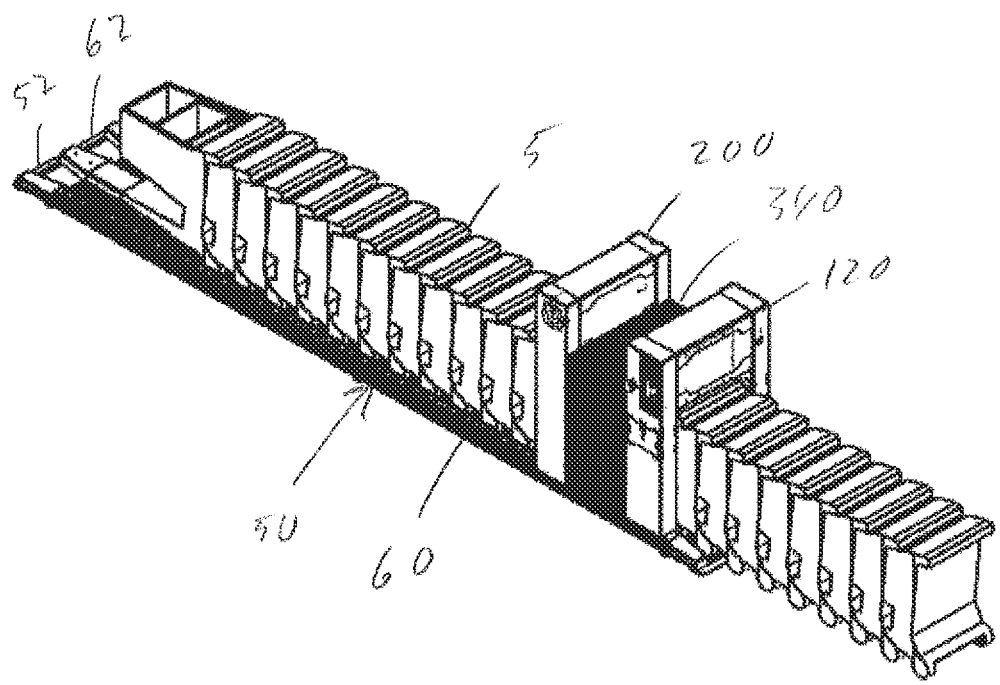
FIG. 34 is similar to FIG. 33 but shows a batch of carts ready to be processed.

In FIG. 34, a sufficient number of carts is advanced onto the foundation 60 for a batch of cleaning. The gantry 200 is in the retracted position at this time.

Figure 35:
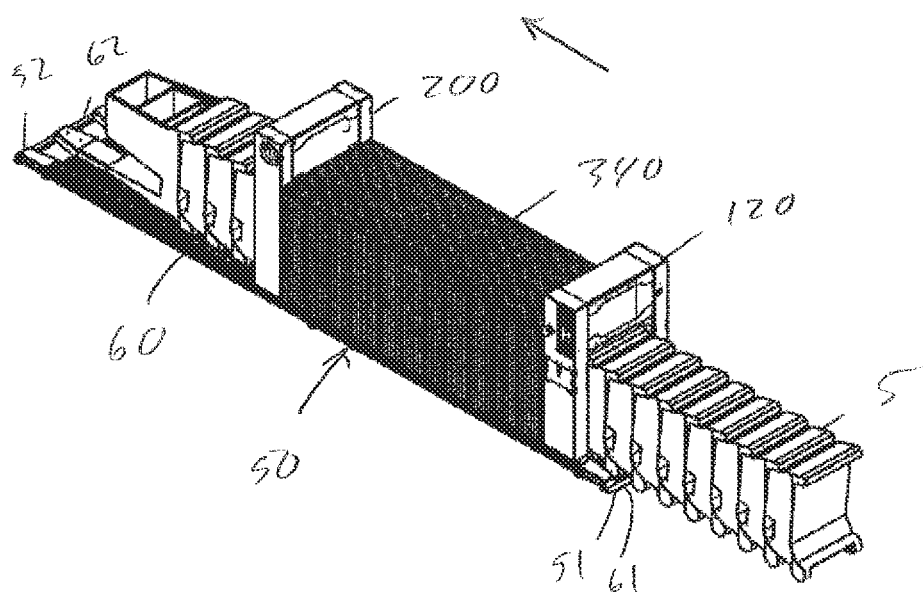
FIG. 35 is similar to FIG. 34 but shows the gantry extending.
Figure 36:
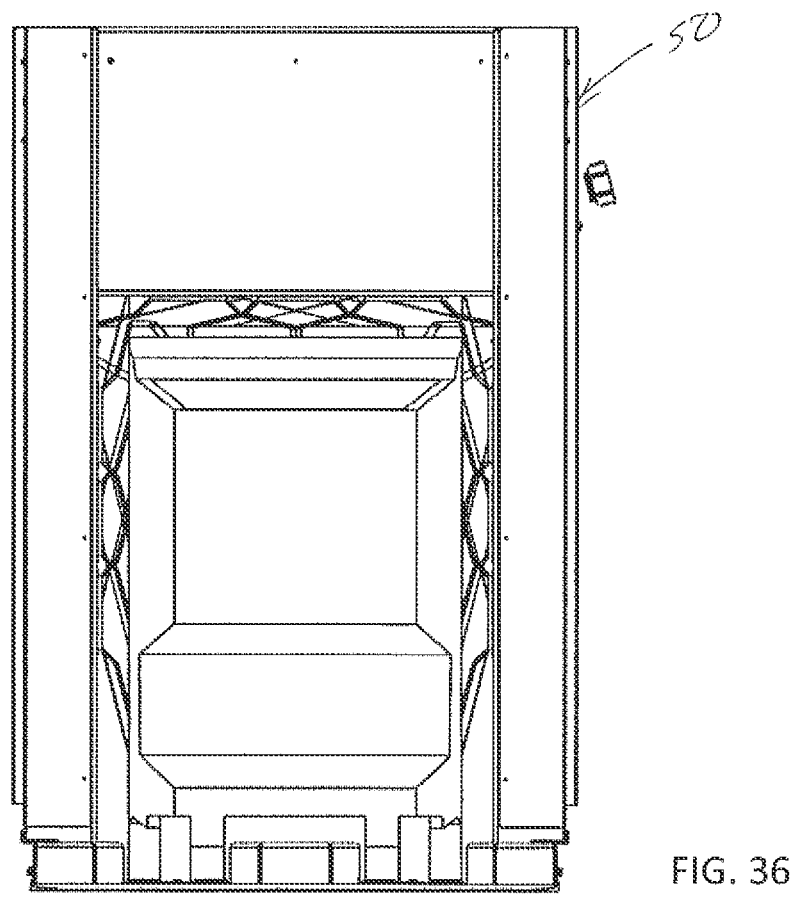
FIG. 36 is an end view of the embodiment illustrated in FIG. 35 showing spray patterns of the nozzles upon the carts being processed.

In FIG. 35, the gantry 200 is extending towards end 52 of the cleaner. The gantry moves as the movement mechanism 250 interacts with the bands 310 and 320. The nozzles 220 are spraying a mixture of chemicals and water onto the carts 5 as the gantry is advanced. It is appreciated that the blowers 230 and 240 can also be operational to enhance air turbulence and increase liquid coverage. The recoilers have springs that wind as lines are extended from the recoilers (unwinding from a shaft) as the gantry moves away from the dock. An exemplary nozzle spray pattern is illustrated in FIG. 36.

Figure 37:
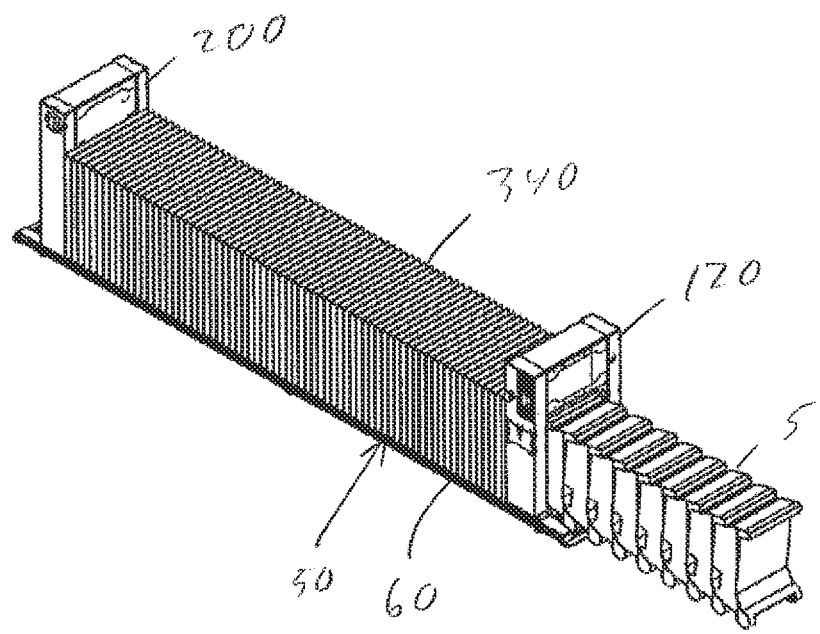
FIG. 37 is similar to FIG. 35 but shows the gantry in the fully extended position.
Figure 38:
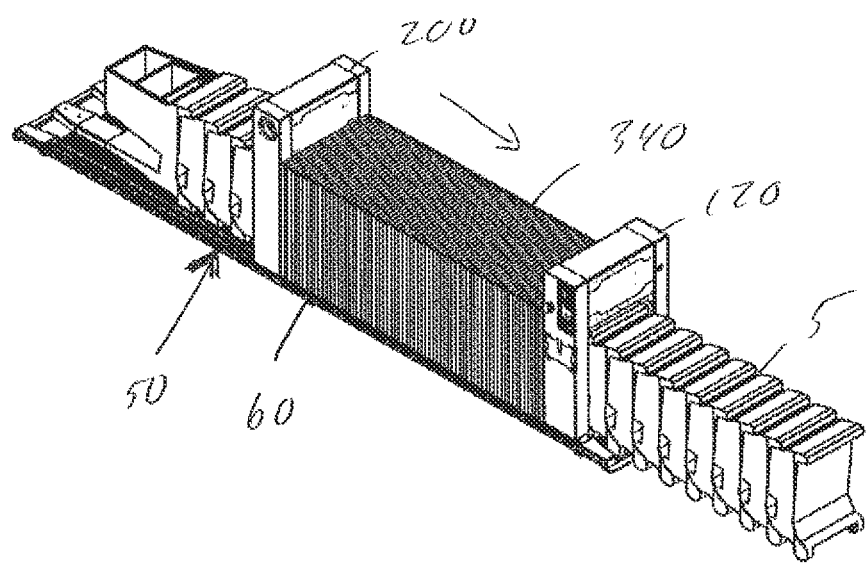
FIG. 38 is similar to FIG. 37 but shows the gantry being retracted towards the dock.
Figure 39:
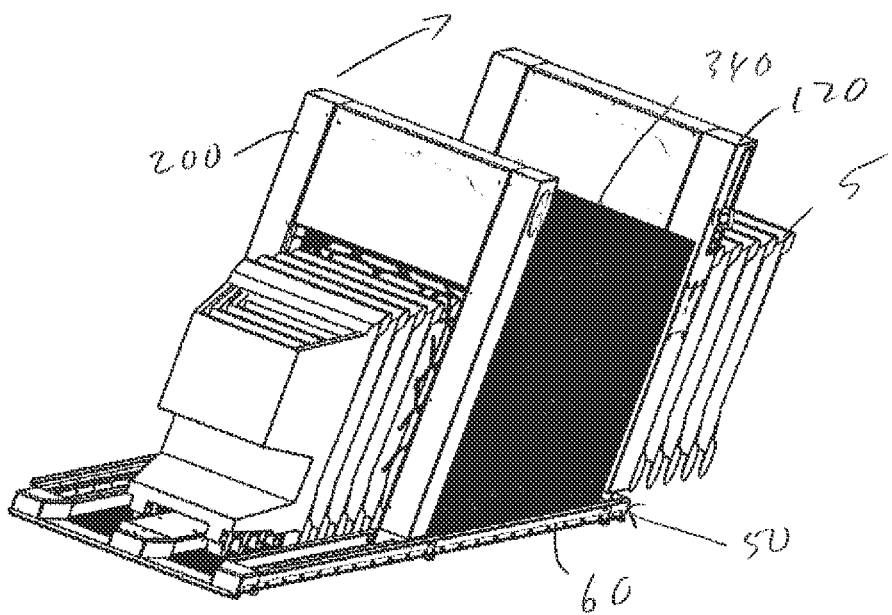
FIG. 39 is an alternative perspective view of the embodiment illustrated in FIG. 38.

Turning to FIG. 37 it is seen that the gantry 200 is fully extended. The spray nozzles 220 and blowers 230 and 240 preferably turn off when the gantry 200 reaches the terminal end of its travel. The gantry 200 can remain extended for a preselected period of time to ensure the chemicals have enough time to disinfect the carts 5. While it is appreciated that zero to several minutes may be preferred, the actual time during use will be based of the recommended disinfecting time of the disinfectant manufacturer.

Figure 40:
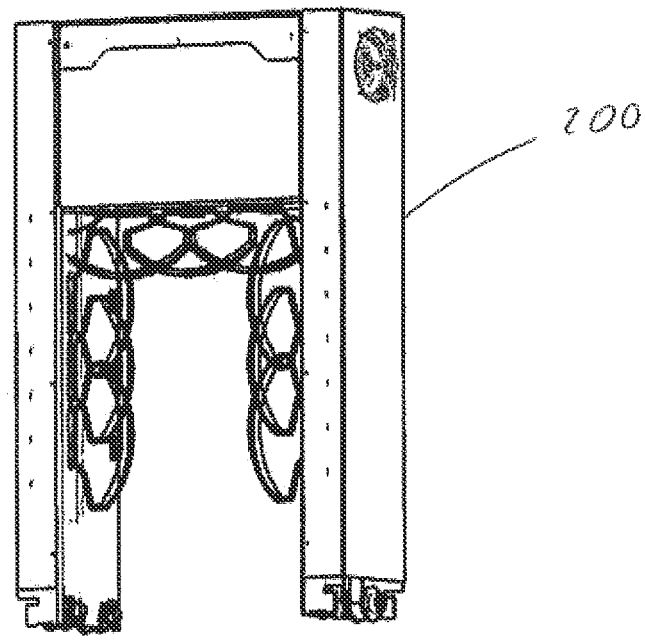
FIG. 40 is an isolation view of the gantry showing the blowing patterns.
Figure 41:
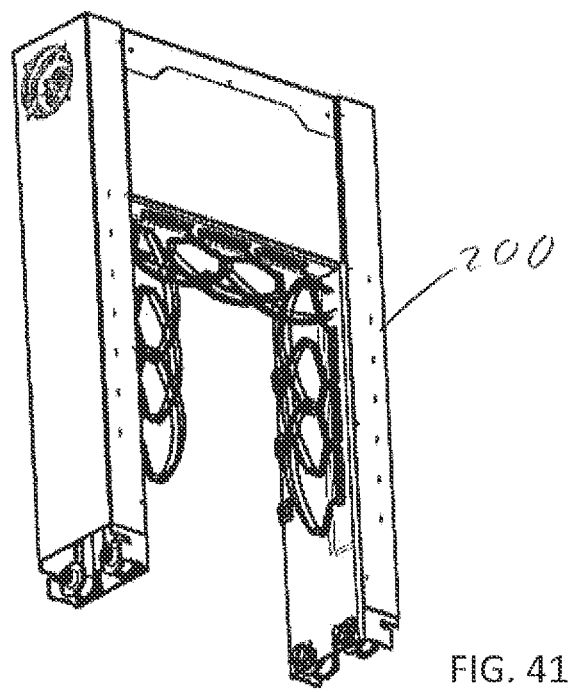
FIG. 41 is a reverse perspective view of the embodiment illustrated in FIG. 40.

The blowers 230 and 240 are again turned on before the gantry 200 begins retracting towards the dock 120. The gantry 200 is shown in this position in FIGS. 38 and 39. In FIGS. 40 and 41, the air blowoff patterns of the openings 232 and 242 are illustrated. The recoiler springs unwind as the gantry moves towards the dock and the lines are rewound in the recoilers.

Figure 42:
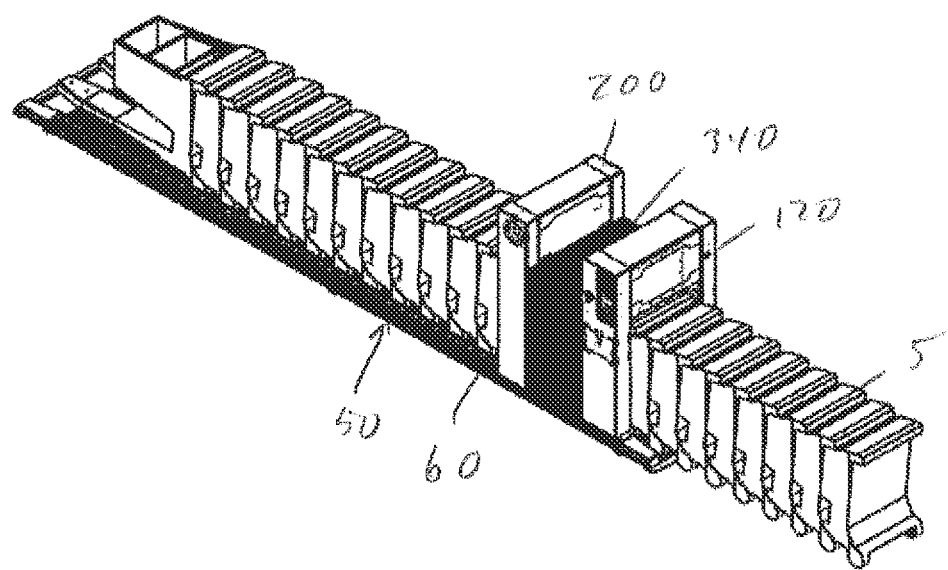
FIG. 42 is similar to FIG. 38 but shows the gantry retracted and a batch of carts processed.

The gantry 200 is illustrated in the fully retracted position in FIG. 42. At this point, the carts 5 have been processed and blown off.

Figure 43:
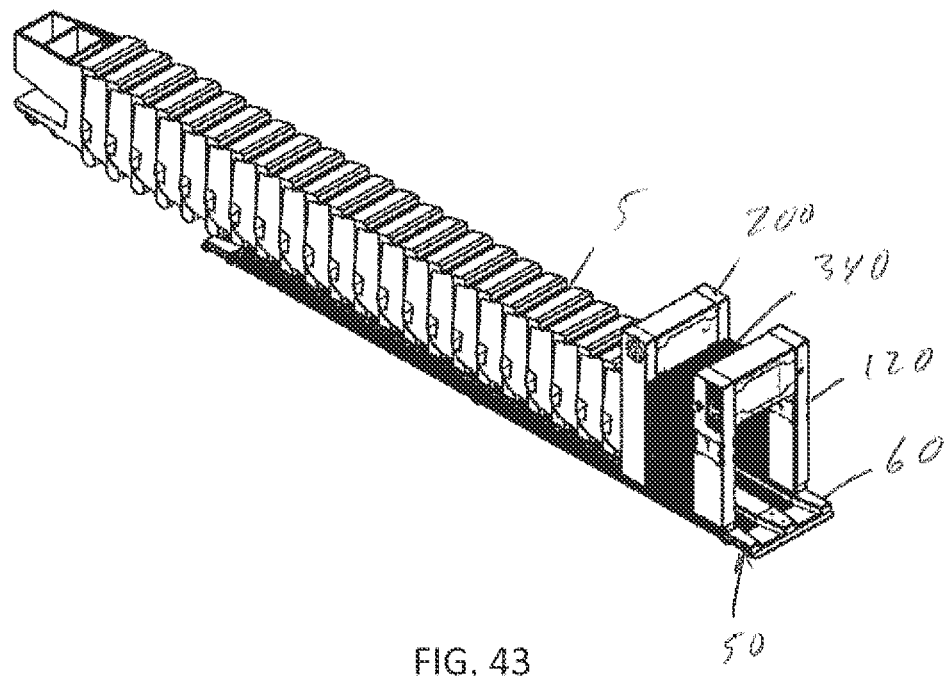
FIG. 43 is similar to FIG. 42 but shows the carts being advanced within the cleaner so that a new batch of carts is ready for processing.
Figure 44:
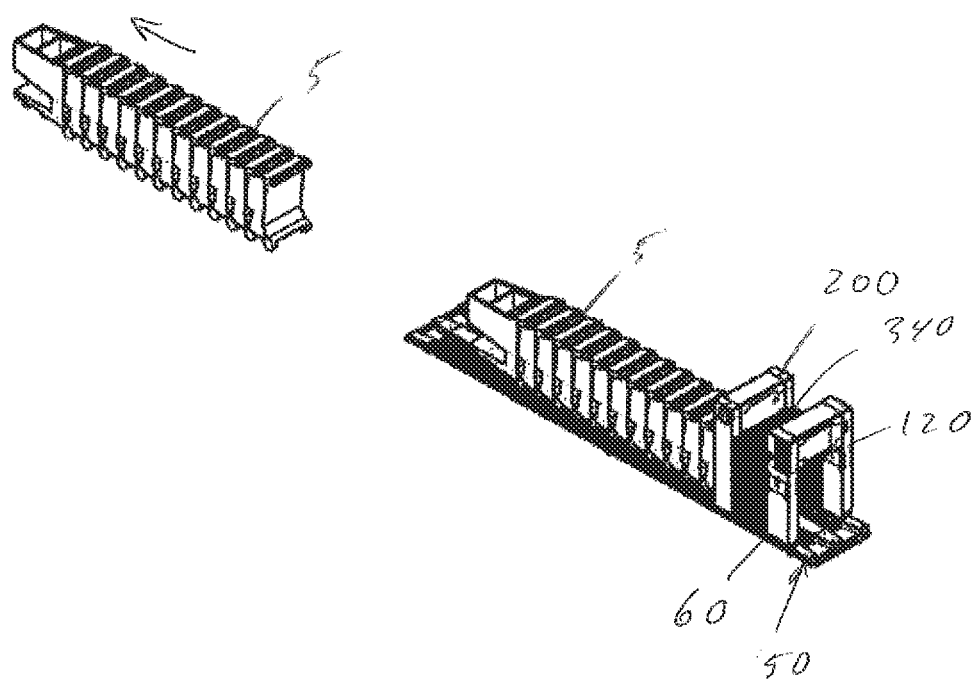
FIG. 44 is similar to FIG. 43 but shows the processed carts removed from the cart processing line.
Figure 45:
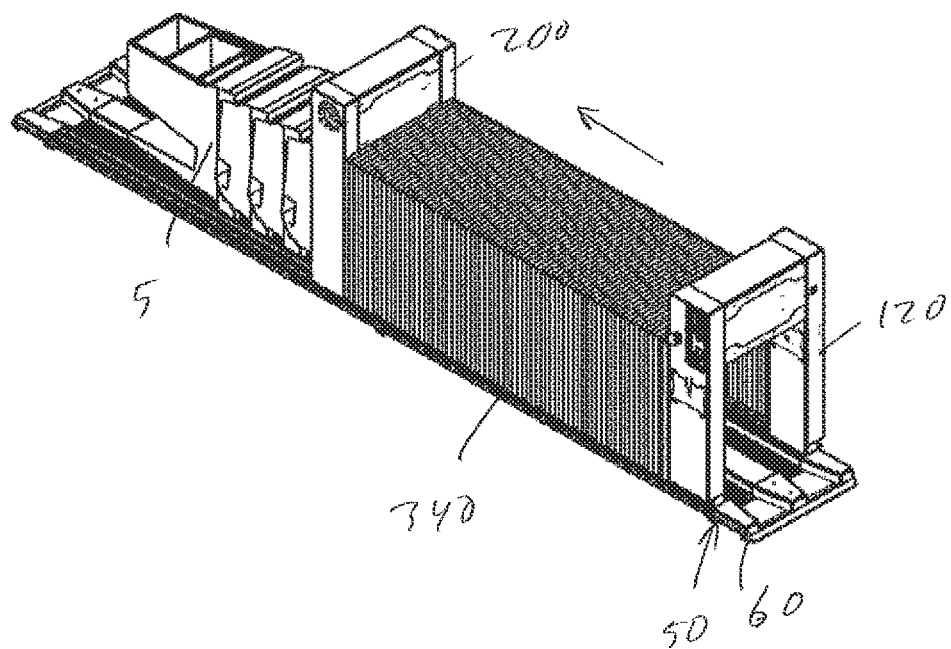
FIG. 45 is similar to FIG. 44 but shows the gantry being extended to process a second batch of carts.
Figure 46:
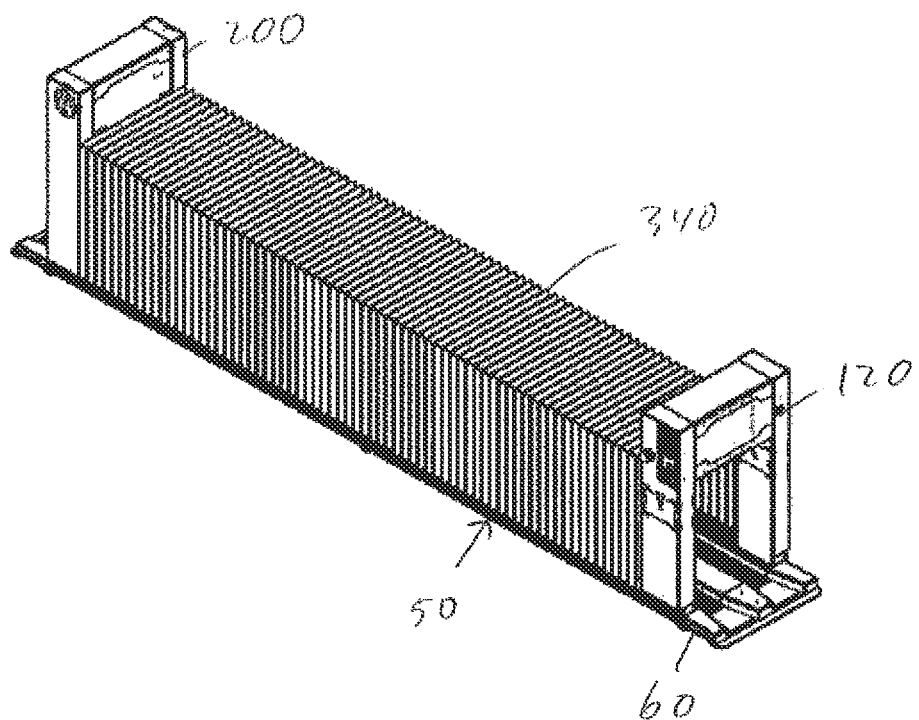
FIG. 46 is similar to FIG. 45 but shows the gantry fully extended.
Figure 47:
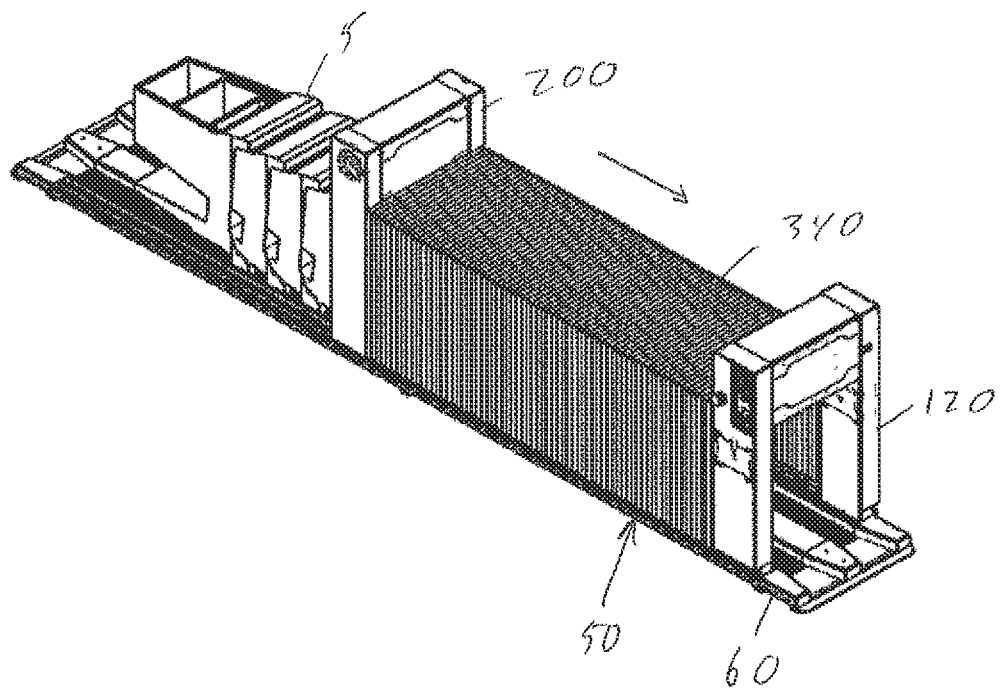
FIG. 47 is similar to FIG. 46 but shows the gantry being retracted.
Figure 48:
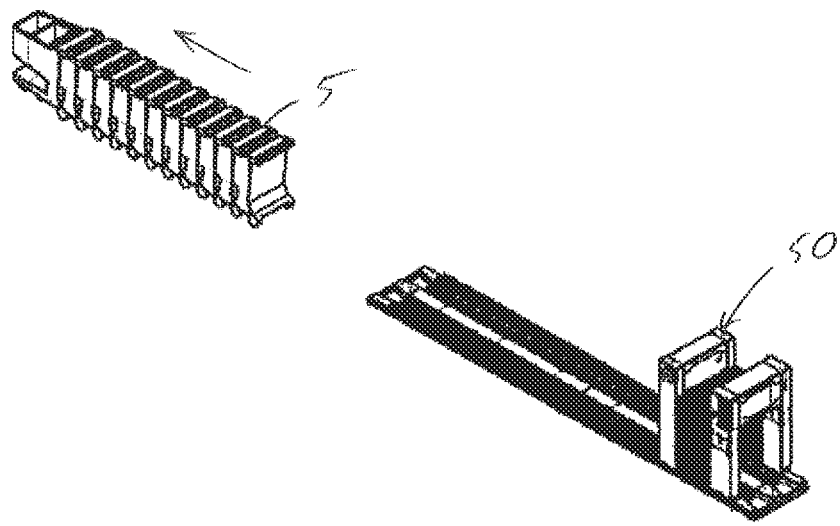
FIG. 48 is similar to FIG. 47 but shows the gantry fully retracted and the processed carts removed from the cleaner.

Carts are then advanced, as shown in FIG. 43. The carts pass over shaker breaks 76 as they are advanced to encourage excess fluid to fall from the carts and onto the absorbent runners 74. The cleaned carts can optionally then be removed from the cleaner as seen in FIG. 44 while another batch of carts is in position to be cleaned. As an alternative, the cleaner can be towards the cart entry end of a corral and processed carts can simply be sequentially pushed forward as batches of carts 5 are cleaned.

FIGS. 45-48 show the processing sequence of another batch of carts 5, the operation of which is similar to the process outlined above.

Figure 49:
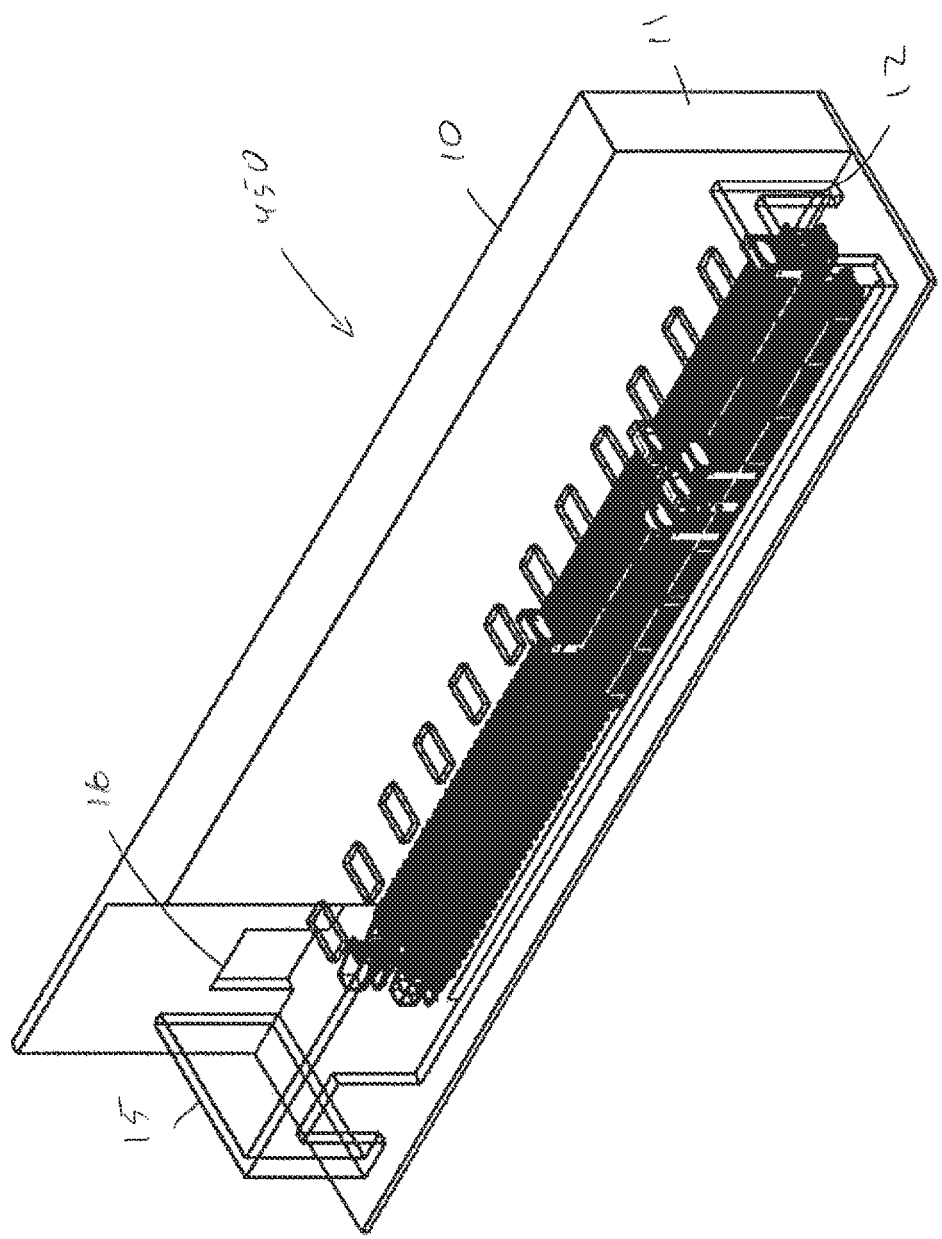
FIG. 49 is a perspective view of an alternative configuration of a preferred embodiment of the present invention having two gantries for each dock station which move in opposite directions from the dock.
Figure 50:
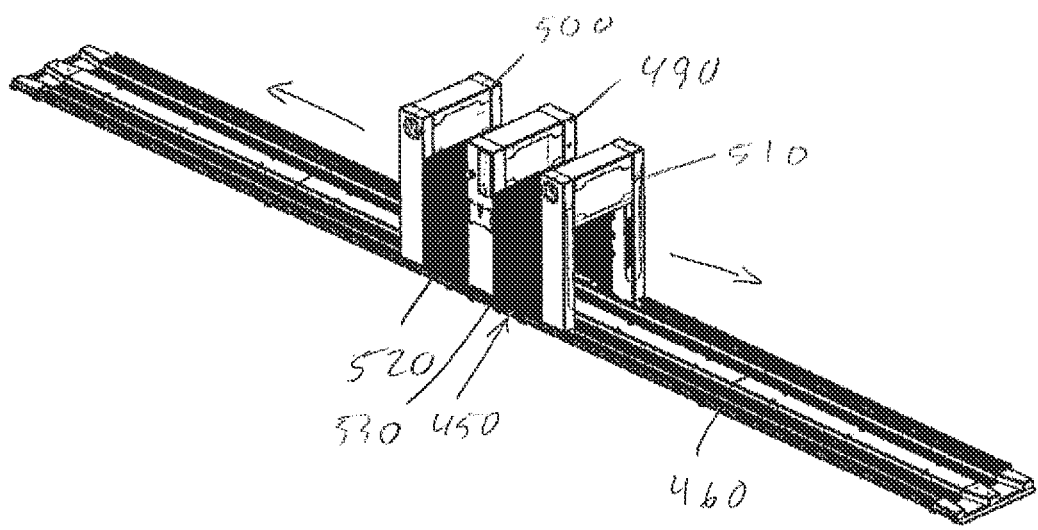
FIG. 50 is a perspective view showing two gantry configuration illustrated in FIG. 49, with the gantries retracted.
Figure 51:
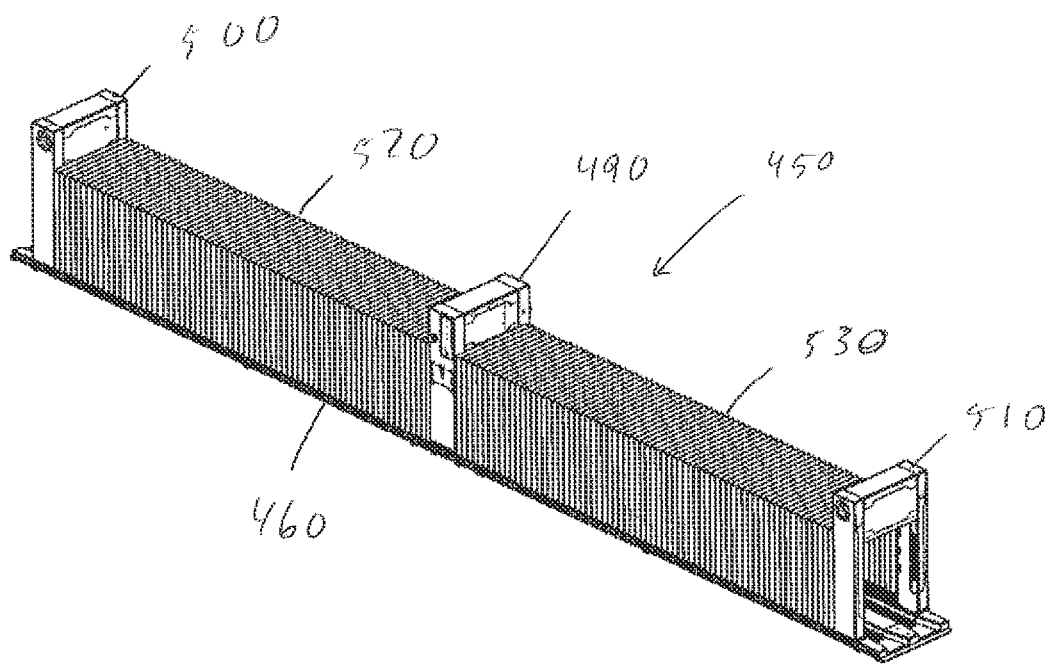
FIG. 51 is similar to FIG. 50 but shows the gantries fully extended.

An alternative layout 450 of the present invention is illustrated in FIGS. 49-51. In this layout 450, which can process an increased number of carts 5 per processing batch, an elongated foundation 460 is provided having enough frame sections to construct a foundation of adequate length. A dock 490 is stationarily connected to the middle of the foundation 460. Then, two movable gantries 500 and 510 are provided to extend in opposite directions from the dock 490 to clean carts in both directions. Two bellow assemblies 520 and 530, respectively, are also provided. Bellow assembly 520 is connected to the dock 490 and to gantry 500. Bellow assembly 530 is connected to dock 490 and to gantry 510. Operation of the gantries may be simultaneous or separate.

Figure 52:
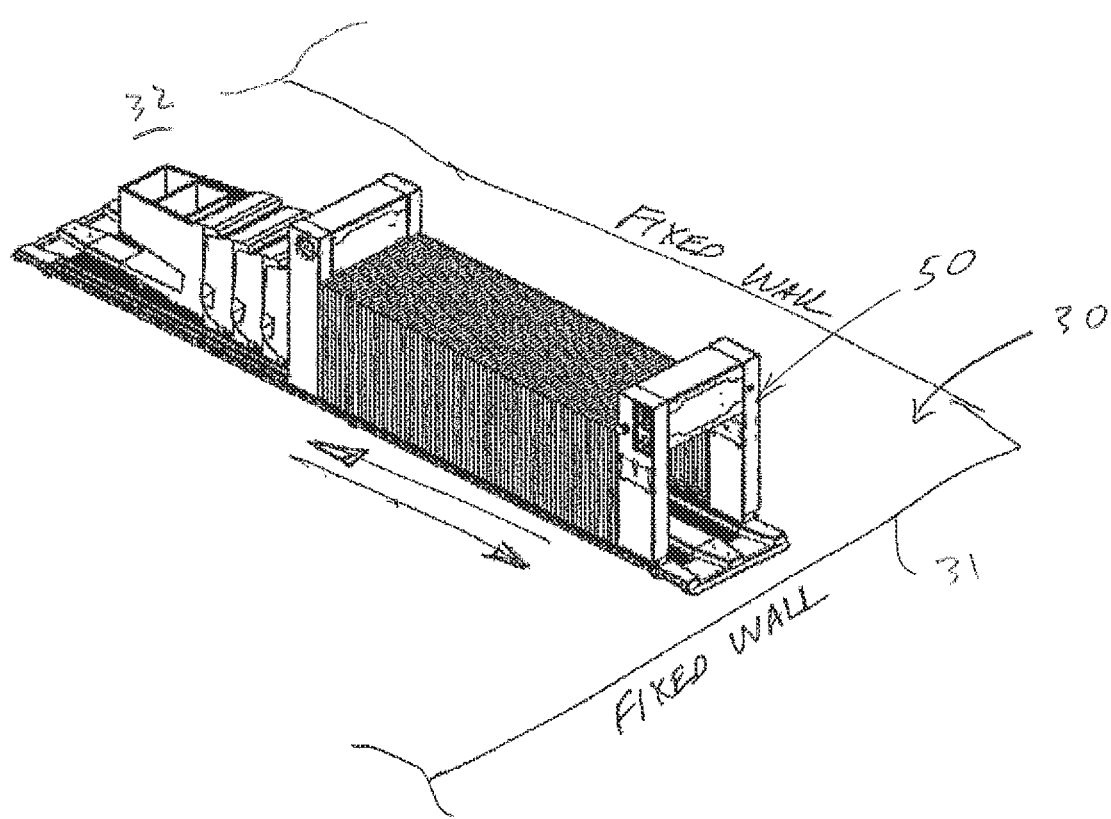
FIG. 52 is an illustration of a configuration with a dead-end cart corral.

Cleaner 50 can also be used in a corral 30 with a dead end 31 and an open end 32 as seen in FIG. 52. In such a corral, there can be one cleaner 50 per row in the dead-end corral 30. Further, the carts can be processed either oriented handle forward or handle rearward relative to the open end 32 of the corral.

The present invention is customizable via the controller 140 for precision control of sanitizing fluid delivery. The speed of the gantry 200, the overall length of the foundation, the cart type and other factors can be considered so that full and consistent processing of carts 5 is achieved with the present invention.

Thus it is apparent that there has been provided, in accordance with the invention, a cart cleaning machine that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. A cart cleaning machine comprising:
   a foundation with a first end and a second end, said foundation being a modular foundation and comprising a plurality of frames comprising a first end frame and a second end frame;
   a dock at a fixed location relative to the foundation that is interior of said first end frame and said second end frame;
   a first gantry, said first gantry being movable between said dock and said second end;
   a bellow between said dock and said first gantry; and
   a second gantry, said first gantry and said second gantry extending in opposite directions from said dock during deployment.

2. The cart cleaning machine of claim 1, wherein:
   said cart cleaning machine further comprises a water line; and
   said dock comprises controller, a water inlet, a chemical station and a water line management device.

3. The cart cleaning machine of claim 2, wherein:
   said dock further comprises a cart opening; and
   said first end of said foundation is a flared first end.

4. The cart cleaning machine of claim 1 wherein said first gantry has a spray nozzle and a blower.

5. The cart cleaning machine of claim 4 wherein said spray nozzle and said blower are operational simultaneously during a cleaning operation, and said blower is operational alone during a drying operation.

6. The cart cleaning machine of claim 1 wherein each of said plurality of frames is comprised of a path, a first side channel, a second side channel, a grate and a shaker break.

7. The cart cleaning machine of claim 1 further comprising a drive guide and a band, said drive guide being atop said foundation.

8. The cart cleaning machine of claim 7 wherein said first gantry comprises a movement mechanism with a motor and a sprocket, said sprocket engaging said band to move said first gantry relative to said drive guide and said foundation.

9. The cart cleaning machine of claim 8 wherein said first gantry further comprises a wheel with an outer flange, said flange engaging a side of said drive guide.

10. The cart cleaning machine of claim 1 wherein said bellow comprises a stiffener.

11. The cart cleaning machine of claim 1 wherein:
    said bellow is a first bellow; and
    said cart cleaning machine further comprises a second bellow being between said dock and said second gantry.

\* \* \* \* \*